(12) United States Patent
McBride et al.

(10) Patent No.: US 11,549,095 B2
(45) Date of Patent: Jan. 10, 2023

(54) METHOD FOR GROWING ALGAE

(71) Applicant: Triton Algae Innovations, San Diego, CA (US)

(72) Inventors: Robert McBride, San Diego, CA (US); Oscar Gonzalez, San Diego, CA (US); Stephen Mayfield, Cardiff, CA (US); Miller Tran, San Diego, CA (US); Xun Wang, San Diego, CA (US); Jon Hansen, San Diego, CA (US)

(73) Assignee: Triton Algae Innovations, Inc., San Diego, CA (US)

( * ) Notice: Subject to any disclaimer, the term of this patent is extended or adjusted under 35 U.S.C. 154(b) by 0 days.

(21) Appl. No.: 16/327,642

(22) PCT Filed: Aug. 14, 2017

(86) PCT No.: PCT/US2017/046831
§ 371 (c)(1),
(2) Date: Feb. 22, 2019

(87) PCT Pub. No.: WO2018/038960
PCT Pub. Date: Mar. 1, 2018

(65) Prior Publication Data
US 2019/0183161 A1 Jun. 20, 2019

Related U.S. Application Data

(60) Provisional application No. 62/379,358, filed on Aug. 25, 2016.

(51) Int. Cl.
| | |
|---|---|
| *C12N 1/12* | (2006.01) |
| *A01G 33/00* | (2006.01) |
| *C12N 15/82* | (2006.01) |
| *A23L 33/195* | (2016.01) |
| *A23L 17/60* | (2016.01) |
| *A23L 33/105* | (2016.01) |
| *C12P 21/02* | (2006.01) |

(52) U.S. Cl.
CPC ............. *C12N 1/12* (2013.01); *A01G 33/00* (2013.01); *A23L 17/60* (2016.08); *A23L 33/105* (2016.08); *A23L 33/195* (2016.08); *C12N 15/8201* (2013.01); *C12N 15/8257* (2013.01); *C12P 21/02* (2013.01); *Y02A 40/90* (2018.01)

(58) Field of Classification Search
CPC ...... A23L 33/195; A23L 29/00; A23L 29/065; C12N 1/12; A01G 33/00; B03D 2203/001; B01J 2220/4843
See application file for complete search history.

(56) References Cited

U.S. PATENT DOCUMENTS

| | | | |
|---|---|---|---|
| 2010/0297296 A1* | 11/2010 | Brooks | A23D 7/001 426/61 |
| 2012/0034653 A1 | 2/2012 | Apt. et al. | |
| 2015/0315538 A1* | 11/2015 | Whitman | C12P 21/00 435/71.2 |
| 2019/0183161 A1 | 6/2019 | McBride et al. | |
| 2020/0370004 A1 | 11/2020 | Tran et al. | |

FOREIGN PATENT DOCUMENTS

| | | |
|---|---|---|
| CN | 1827769 | 9/2006 |
| CN | 101979498 A | 2/2011 |
| CN | 109153965 A | 1/2019 |
| JP | S52-105276 | 9/1977 |
| JP | 2000152778 A | 6/2000 |
| JP | 2019-526282 A | 9/2019 |
| WO | 2011/063284 A1 | 5/2011 |
| WO | 2013100756 A2 | 7/2013 |
| WO | 2014088943 A2 | 6/2014 |
| WO | 2015/126992 A1 | 8/2015 |

OTHER PUBLICATIONS

Rasala, B.A., Mayfield, S., "The microalga Clamydomonas reinhardtii as a platform for the production of human protein therapeutics", Bioengineered Bugs 2:1, 2010, pp. 50-54 (Year: 2010).*
Khan, M., Karmakar, R., Das, B., Diba, F., Razu, M., "Heterotrophic Growth of Micro Algae", Feb. 2016, Recent Advances in Microalgal Biotechnology, pp. 1-18 (Year: 2016).*
Martin, G.A., Hempfling, W.P., "A Method for the Regulation of Microbial Population Density during Continuous Culture at High Growth Rates", 1976, Archives of Microbiology, vol. 107, pp. 41-47 (Year: 1976).*
Boyle, N.R., Morgan, J.A., "Flux balance analysis of primary metabolism in Chlamydomonas reinhardtii", 2009, BMC Systems Biology (Year: 2009).*
Moheimani et al., "Harvesting and dewatering of high-productivity bulk microalgae systems", May 2016, Micro-algal production for biomass and high-value products, pp. 253-266 (Year: 2016).*
Gerson et al., "Substrate Concentration Control in Bioreactors", 1988, Biotechnology and Genetic Engineering Reviews, vol. 6:1, pp. 67-150 (Year: 1988).*
PH auxostat, 2010, University of Maryland Baltimore County (UMBC), https://userpages.umbc.edu/~xkang/ENCH772/phauxostat.htm (Year: 2010).*
PCT/US2017/046831 International Search Report and Written Opinion dated Jan. 17, 2018.
De Swaaf et al. "High-Cell-Density Fed-Batch Cultivation of the Docosahexaenoic Acid Producing Marine Alga Crypthecodinium Cohnii." Biotechnology and Bioengineering, 2003, 81(6):666-672.

(Continued)

*Primary Examiner* — Jeffrey P Mornhinweg
*Assistant Examiner* — Kelly P Kershaw
(74) *Attorney, Agent, or Firm* — Mandar A. Joshi; Bozicevic, Field & Francis LLP

(57) ABSTRACT

Provided herein are methods for the production of high density cultures of algae as well as nutritional supplements from such cultures and the use of such cultures to produce therapeutic proteins.

28 Claims, 12 Drawing Sheets

(56) References Cited

OTHER PUBLICATIONS

Chen, F. et al. "High Cell Density Culture of Chlamydomonas Reinhardtii on Acetate Using Fed-Barch and Hollow-Fibre Cell-Recycle Systems." Bioresource Technology, 1996, 55:103-110.
EP17844134.1 Extended European Search Report dated Mar. 9, 2020.
Bumbak et al. "Best Practices in Heterotrophic High-Cell-Density Microalgal Processes: Achievements, Potential and Possible Limitations." Applied Microbiology and Biotechnology, May 13, 2011, 91(1):31-46.
Chen et al. "Heterotrophic Growth of Chlamydomonas Reinhardtii on Acetate in Chemostat Culture." Process Biochemistry, Aug. 1, 1996, 31(6):601-604.
Rasala et al. "Production of Therapeutic Proteins in Algae, Analysis of Expression of Seven Human Proteins in the Chloroplast of Chlamydomonas Reinhardtii." Plant Biotechnology Journal, Aug. 7, 2010, 8(6):719-733.
Perez-Garcia et al. "Heterotrophic Cultures of Microalgae: Metabolism and Potential Products." Water Research, Jan. 1, 2011, 45(1):11-36.
Doron et al. "Transgene Expression in Microalgae—From Tools to Applications." Frontiers in Plant Science, Apr. 22, 2016, 7(505):1-24.
Zhang et al. "Efficient Heterotrophic Cultivation of Chlamydomonas Reinhardtii" Journal of Applied Phycology, 2019, 31(3):1545-1554.
Chen, Feng, (1996) "High cell density culture of microalge in heterotrophic growth", Trends in Biotechnology, 14:421 426.
PCT/US2018/060830 International Search Report and Written Opinion dated Feb. 7, 2019.
Doebbe et al., (2007) "Functional Integration of the HUP1 hexose symporter gene into the genome of C. reinhardtii: Impacts on Biological H2 Production", Journal of Biotechnology, vol. 131, pp. 27-33.
Hasan et al., (2014) "Bioremediation of Swine Wastewater and Biofuel Potential by using Chlorella vulgaris, Chlamydomonas reinhardtii, and Chlamydomonas debaryana", Journal of Petroleum & Environment Biotechnology, vol. 5, No. 175, pp. 1-20.
Torres-Tiji, Yasin, et al., (2022) "Optimized production of a bioactive human recombinant protein from the microalgae Chlamydomonas reinhardtii grown at high density in a fed-batch bioreactor". Algal Research, 66:1-8.

\* cited by examiner

METHOD FOR GROWING ALGAE

CROSS REFERENCE TO RELATED APPLICATIONS

This application is a US national phase application under 35 USC § 371 of international application no. PCT/US2017/046831, filed Aug. 14, 2017, which claims the benefit of priority under 35 USC § 119(e) of U.S. Ser. No. 62/379,358, filed Aug. 25, 2016, the entire content of each of which is incorporated herein by reference.

BACKGROUND

As the world's population continues to grow, there is an increasing demand for edible sources of protein. This demand will need to be met despite the fact that the land suitable for the cultivation of traditional crops is limited. Algae provide an alternative to traditional agricultural crops. Algae have several advantages over terrestrial crops. Algae reproduce at a very high rate with a generation time as short as 10 hours. Many strains of algae are also high in protein, with some strains of blue green algae reported to be as much as 70% protein (Becker, *Biotech. Adv.* (2007) 25:207). The rapid reproduction rate of algae combined with a high protein content means that algae can produce more than 10 times more protein than soybeans on a per acre basis.

Algae are especially useful for the production of edible protein for humans and non-ruminant animals, because in addition to the large quantities of protein that can be produced, the protein is also of high quality in terms of its amino acid composition. The amino acid composition of algae is similar to that found in other high quality plant sources such as soy and far superior to cereal grains such as wheat (Fabregas and Herrero, *Applied Microbiol. Biotechnol.* (1985) 23:110). Algal protein has a relatively high biological value, comparing favorably to animal proteins such as eggs and casein (Becker, supra). In addition, algal protein is highly digestible. Additionally, algae may be genetically engineered to produce proteins of a particular nutritional value.

In addition to its use as a source of nutritional protein, algae are also useful for the production of therapeutic proteins. Protein based therapeutics are an increasingly important aspect of medical treatment. Interest in eukaryotic microalgae as an alternative platform for recombinant protein production has been gaining in recent years. Protein production in transgenic algae can offer many of the same advantages as transgenic plants, including cost, safety, and rapid scalability. Microalgae expressing therapeutic proteins can be grown under the improved conditions described herein. Expression of recombinant proteins in the chloroplast of the green algae *Chlamydomonas reinhardtii* is well established (Mayfield S. P., et al. (2007) *Curr Opin Biotechnol* 18:126433). These proteins include reporter proteins (Franklin S., et al, *Plant J.* (2002) 30:733-744; Mayfield S. P. and Schultz J. *Plant J.* (2004) 37:449-458; Muto M., et al. *BMC Biotechnol* (2009) 9:26), a large complex mammalian single chain antibody (Mayfield S. P., et al. *Proc Natl Acad Sci USA* (2003) 100:438-442), more traditional single chain antibodies (Franklin S. E. and Mayfield S. P. *Expert Opin Biol Ther.* (2005) 5:225-235), a full length monoclonal antibody (Tran M., et al. *Biotechnol Bioeng.* (2009) 104(4): 663-673), potential vaccine antigens (Surzycki R., et al. *Biologicals* (2009) 37:133-138), and a variety of potential therapeutic proteins (Rasala et al. *Plant Biotechnol. J.* (2010) 8:719-733). Proteins purified from algae have advantages over those produced in standard processes because they should be free from toxins and viral agents that may be present in preparations from bacteria or mammalian cell culture.

An important factor impeding the wide spread use of algae as a protein source and a production platform for therapeutic proteins is the high cost of production. Algae for human consumption or pharmaceutical use must be produced to high quality standards. In most cases, the algae must be grown in enclosed fermentation vessels. The use of enclosed fermentation vessels increases the cost of production both in terms of large amounts of capital required to purchase and install the fermentors, and the high energy costs associated with running the fermentors.

One way to decrease the cost of production is to increase the growth rate of the algae. With higher growth rates, the capital and operating cost are spread over a larger amount of product, thus reducing the per unit cost of production. Provided herein is an improved method of producing algae which results in substantially higher growth rates and an improved nutritional profile.

SUMMARY

Among the several aspects and embodiments of the inventive concepts disclosed herein include: a method for the aerobic, heterotrophic cultivation of a high density culture of a *Chlamydomonas* species wherein the culture achieves a target density of between 50 and 200 g/L dry cell weight. In certain embodiments, the culture achieves a target density of at least 50 g/L, at least 60 g/L, at least 70 g/L, at least 80 g/L, at least 90 g/L, at least 100 g/L, at least 110 g/L, at least 120 g/L, at least 130 g/L, at least 140 g/L, at least 150 g/L, at least 160 g/L, at least 170 g/L, at least 180 g/L, at least 190 g/L or at least 200 g/L dry cell weight. In other embodiments, the target density is between 50 and 75 g/L, between 75 and 100 g/L, between 100 and 125 g/L, between 125 and 150 g/L, between 150 and 175 g/L or between 175 and 200 g/L dry cell weight. In certain embodiments the production culture is grown to a density of 50 g/L, 55 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L or 200 g/L dry cell weight before harvesting. In some embodiments, the target density or concentration is reached within 250 hours after the start of the production culture.

The *Chlamydomonas* sp. used can be any species that is capable of heterotrophic or mixotrophic growth, for example *Chlamydomonas reinhardtii*, *Chlamydomonas dysomos*, *Chlamydomonas mundane*, *Chlamydomonas debaryana*, *Chlamydomonas moewusii*, *Chlamydomonas culleus*, *Chlamydomonas noctigama*, *Chlamydomonas aulata*, *Chlamydomonas applanata*, *Chlamydomonas marvanii*, or *Chlamydomonas proboscigera*. In one embodiment, the *Chlamydomonas* sp. is a wild-type species, that is, it does not contain a heterologous or exogenous gene.

The method comprises obtaining inoculum of a substantially pure culture of a *Chlamydomonas* sp. at a concentration of 0.1 to 15 g/L. The inoculum is used to produce a production culture by adding it to an initial volume of fermentation medium where the amount of inoculum used does not exceed 20% of the initial volume of fermentation medium. The production culture is then grown aerobically at a pH of between about 6.0 and 10.0, and at a temperature of about 15° C. to about 37° C. In one embodiment, the production culture is grown in the absence of light. In one method, the production culture is fed by providing feeding medium which is a 100× concentration of the fermentation medium supplemented with glacial acetic acid. The feeding schedule is determined by a change in the pH of the production culture. The production culture is grown until it reaches the desired target density at which point the algae are harvested from the culture.

In certain embodiments, the production culture is fed when the pH of the production culture increases beyond a pre-determined set point. In some embodiments feeding is commenced when the pH exceeds 7.5 and is discontinued after the pH decreases below 6.8. In other embodiments feeding is used to maintain the pH of the production culture at pH 6.6±0.1, pH 6.8±0.1 or pH 7.0±0.1.

Harvesting may be accomplished by any method known in the art, including, but not limited to filtration, batch centrifugation or continuous centrifugation. In some instances, the production culture reaches the harvest density within 250 hours of the start of the culture.

The harvested algae may be dried, for example to a moisture content of not more than 15% by spray drying, ring drying, paddle drying, tray drying, solar or sun drying, vacuum drying, or freeze drying.

Another aspect provides a nutritional supplement comprising at least 90% of at least one *Chlamydomonas* sp. where the nutritional supplement is not more than 15% moisture, at least 50% crude protein, at least 10% fat and not more than 5% ash. In certain embodiment, the nutritional supplement also contains Omega 3, Omega 6 and Omega 9 fatty acids.

In one aspect is provided a culture of one or more species of *Chlamydomonas* algae under growth conditions where the density of the culture increases at a rate of between 50% and 300%, between 50% and 100%, between 100% and 150%, between 150% and 200%, between 200% and 250% or between 250% and 300% per 24 hour period.

In one aspect is provided a culture of one or more species of *Chlamydomonas* algae under growth conditions where the density of the culture increases at least 50%, at least 75%, at least 100%, at least 125%, at least 150%, at least 175%, at least 200%, at least 225%, at least 250%, at least 275% or at least 300% per 24 hour period.

Also provided is an algal culture of one or more species of *Chlamydomonas* algae under steady state conditions where the culture has a density of algae of at least 50 g/L, at least 60 g/L, at least 70 g/L, at least 80 g/L, at least 90 g/L, at least 100 g/L, at least 110 g/L, at least 120 g/L, at least 130 g/L, at least 140 g/L, at least 150 g/L, at least 160 g/L, at least 170 g/L, at least 180 g/L, at least 190 g/L or at least 200 g/L dry cell weigh, where steady state is defined as a state where the concentration of algae in the culture is increasing between about 0.1% and about 50% per 24 hour period.

Additional aspects provide a method for producing a therapeutic protein from a substantially pure culture of at least one *Chlamydomonas* sp. expressing at least one exogenous therapeutic protein. The method comprises inoculating a production culture with an inoculum comprising the substantially pure culture containing about 0.1 to about 15 g/L of at least one *Chlamydomonas* sp. expressing at least exogenous therapeutic protein. The amount of inoculum used does not exceed 20% of the initial volume of the production culture. The production culture is then grown aerobically at a pH between about 6.4 and 10, and a temperature between about 15° C. and about 37° C. In one embodiment, the production culture is grown in the absence of light. The production culture is fed on a schedule based on the pH of the production culture using a feed medium which is a 100× concentration of the production culture medium supplemented with glacial acetic acid. The production culture is grown until the algae reach the desired target concentration and then the algae are harvested from the medium. The harvesting may be done by filtration, batch centrifugation or continuous centrifugation.

In certain embodiments, the feeding is determined based on an increase in the pH of the production medium. In certain embodiments the production culture is fed if the pH is greater than 7.4 and stops when the pH reaches 6.8. In other embodiments, the feeding schedule is designed to that the pH of the production medium is maintained at pH 6.6±0.1 pH 6.8±0.1 or pH 7.0±0.1.

In some embodiments, the target concentration is at least 65 g/L or at least 70 g/L. In other embodiments, the target concentration is 75 g/L, 80 g/L, 90 g/L, 95 g/L, 100 g/L, 105 g/L, 110 g/L, 115 g/L, 120 g/L, 125 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L. or 200 g/L.

In some embodiments, the algae is dried after harvesting by, for example, spray drying, ring drying, paddle drying, tray drying, solar or sun drying, vacuum drying or freeze drawing. In still other embodiments the method further comprises isolating the at least one therapeutic protein from the algae.

BRIEF DESCRIPTION OF THE DRAWINGS

These and other features, aspects, and advantages of the claimed invention will become better understood with regard to the following description, appended claims and accompanying figures where:

DETAILED DESCRIPTION

Figure 1:
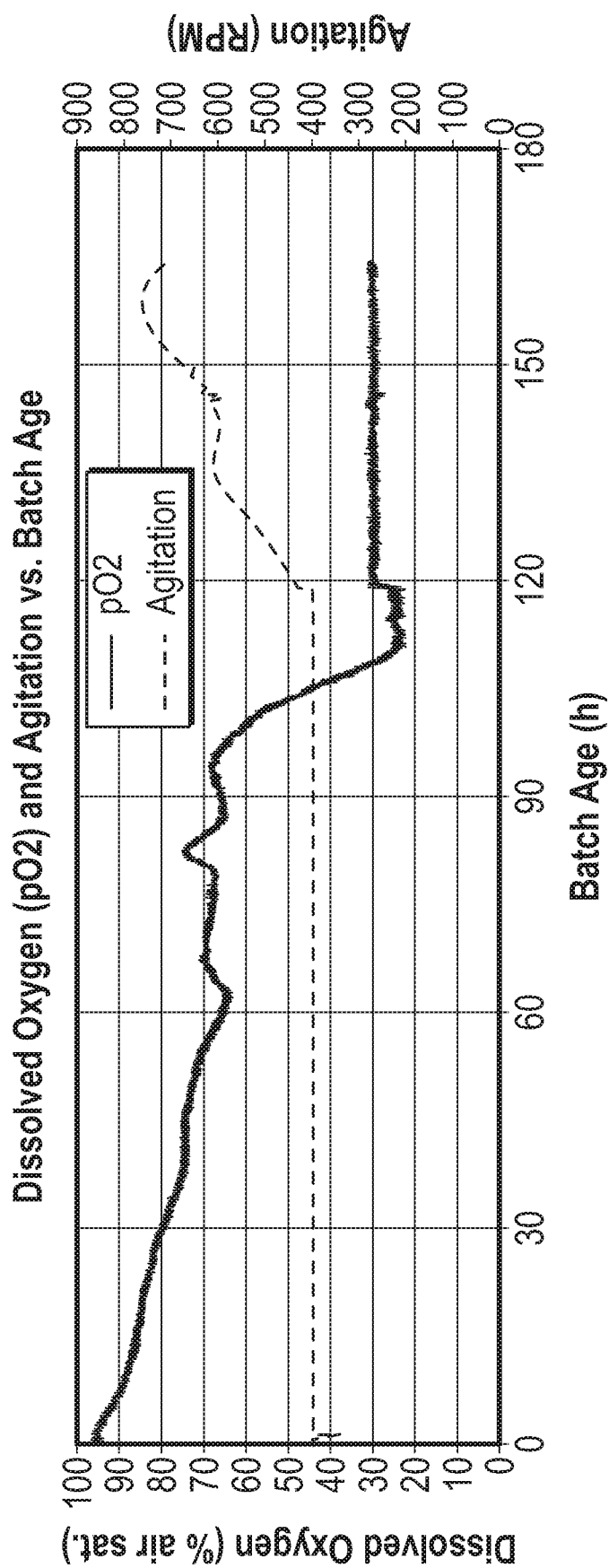
FIG. 1 is a graph of percent saturation of oxygen and agitation vs. batch age in a seed fermentor.

The following detailed description is provided to aid those skilled in the art in practicing the claimed invention. This detailed description should not, however, be construed to unduly limit the claimed invention as modifications and variations in the embodiments discussed herein can be made by those of ordinary skill in the art without departing from the scope of the present inventive discovery.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

As used in this specification and the appended claims, the singular forms "a", "an" and "the" include plural reference unless the context clearly dictates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges can independently be included or excluded in the range, and each range where either, neither or both limits are included in the smaller ranges is also encompassed, subject to any specifically excluded limit in the stated range. Where the stated range includes one or both of the limits, ranges excluding either or both of those included limits are also included. Unless noted otherwise, culture densities or concentrations are on a dry cell weight (DCW) basis.

Provide herein is an improved method for the heterotrophic or mixotropic, aerobic production of algae of the genus *Chlamydomonas*. As used herein, the terms heterotrophic and heterotrophy refer to the situation in which algae can utilize organic carbon source as a source of energy and as a source of carbon. Thus, heterotrophic algae can be grown in the absence of light. As used herein, the terms mixotrophic and mixotrophy refer to the situation in which algae are grown under conditions in which light (photosynthesis) and organic carbon can be used as energy sources. Under mixotrophic conditions, algae can grow by carrying out photosynthesis using light as an energy source to fix inorganic carbon (e.g. carbon dioxide, bicarbonate and/or carbonate) and by heterotrophic growth using organic carbon as an energy source.

Any species of *Chlamydomonas* that is capable of utilizing an organic carbon source as a source of energy can be utilized in practicing the methods disclosed herein. The algae may be strictly heterotrophic in that it is incapable of photosynthesis either naturally or due to genetic manipulation by any means available in the art. By genetic manipulation is meant a change in the genetic make-up of the organism through the manipulation of man. As used herein genetic manipulation includes both recombinant DNA techniques and traditional plant breeding techniques. If traditional plant breeding techniques are utilized, photosynthetic algae can be made strictly heterotrophic by, for example, selection and random mutagenesis. If recombinant DNA techniques are used, the algae can be rendered incapable of photosynthesis by any technique known in the art, for example, gene knock out or gene silencing techniques. One of skill in the art can readily conceive of various methods to render algae incapable of photosynthesis.

Alternatively, the algae may be mixotrophic, either naturally or through the use of genetic manipulation. Examples of species of *Chlamydomonas* that are naturally mixotrophic include, but are not limited to, *Chlamydomonas reinhardtii, Chlamydomonas dysomos, Chlamydomonas mundane, Chlamydomonas debaryana, Chlamydomonas moewusii, Chlamydomonas culleus, Chlamydomonas noctigama, Chlamydomonas aulata, Chlamydomonas applanata, Chlamydomonas marvanii*, and *Chlamydomonas proboscigera*. For example, photosynthetic species of algae which are not naturally heterotrophic can be made so by the use of, for example, by the application of selection pressure. Alternatively, photosynthetic algae may be made heterotrophic by introduction of metabolic pathway genes necessary to metabolize exogenous organic carbon sources through the use of recombinant DNA techniques known in the art.

Whether grown under heterotrophic or mixotrophic conditions, the algae are provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or any organism-specific requirement. Organic carbon sources include any source of carbon which the algae are able to metabolize including, but not limited to, acetate, simple carbohydrates (e.g., glucose, sucrose, lactose), complex carbohydrates (e.g., starch, glycogen), proteins, and lipids. In one embodiment, the carbon source is acetate provided in the form of acetic acid.

The algae used in practicing the methods disclosed herein may be a single species of *Chlamydomonas* or a mixture of species. In one embodiment, the culture contains predominately one species of *Chlamydomonas*. As used herein a culture is predominately one species when that species comprises more than 50% of the algal organisms present. For example, a culture that contains greater than 50%, greater than 55%, greater than 60%, greater than 70%, greater than 80% or greater than 90% of a particular species of *Chlamydomonas* is said to predominately comprise that species. In other embodiments the culture is axenic in terms of either species or genus. As used herein, a culture is said to be axenic for a genus or species if it is free from contamination by organisms other than those intended. For example, a culture that is axenic for *Chlamydomonas* may contain algae of one or more species of *Chlamydomonas* but may not contain organisms of any other genera. Likewise, a culture that is axenic for *Chlamydomonas reinhardtii* may not contain organisms other than *Chlamydomonas reinhardtii*, including other species of *Chlamydomonas*. Methods for determining whether a culture is axenic, for example contaminated by yeast or bacteria, are known by those of skill in the art.

In one embodiment the culture is free of fungi or bacteria as determined by standard methods. In certain embodiments, the culture is free of aerobic bacteria as determined by the absence of colony forming units (CFU). In another embodiment, the culture is free of yeast, mold, and coliform bacteria as determined by the absence of colony forming units. It still other embodiments, the culture is free of *Escherichia coil, Staphylococcus aureus* and *Salmonella* sp. as determined by the absence of colony forming units.

Using the methods disclosed herein, algae are grown heterotrophically or mixatrophically in a bioreactor. The term bioreactor refers to a system closed to the environment and having no direct exchange of gases and contaminants with the environment. In instances where the algae are mixotrophic they can be grown in a photobioreactor. A photobioreactor is a bioreactor which incorporates some type of light source to provide photonic energy input into the reactor. A photobioreactor can be described as an enclosed, illuminated culture vessel designed for controlled biomass production of phototrophic liquid cell suspension cultures. Examples of photobioreactors include, for example, glass containers, plastic tubes, translucent tanks, plastic sleeves, and plastic bags. Examples of light sources that can be used to provide the energy required to sustain photosynthesis include, for example, fluorescent bulbs, LEDs, and natural sunlight.

In certain embodiments, the algae are grown heterotrophically in the absence of light in which case a bioreactor which is not a photobioreactor may be used. In one embodiment, the bioreactor is made out of an opaque material, for example stainless steel, that does not allow for light to enter the interior of the bioreactor. In another embodiment, the bioreactor is made out of a material that allows the passage of light into the interior, such as with a photobioreactor, but the bioreactor itself is contained in an enclosure, such as a room or cabinet that prevents light from entering the bioreactor. In yet another embodiment, a photobioreactor is covered with an opaque material to prevent light from entering.

Regardless of whether light is allowed to enter the interior of the bioreactor, there are several features that may be present in the bioreactor. In one embodiment, the bioreactor is constructed of a material that allows for sterilization of the interior of the bioreactor. Methods that may be used for sterilization include, heat sterilization, chemical sterilization or a combination of the two. The bioreactor may also optionally have heating and cooling elements that allow for the contents of the bioreactor to be held within a desired temperature range. Various methods for controlling the temperature of bioreactors are well known in the art.

In addition, the bioreactor may have methods for controlling the oxygen content of the medium contained in the bioreactor. Oxygen can be introduced into the culture medium using pure oxygen, ambient air or a mixture of pure oxygen and ambient air. Oxygen can be introduced into the medium by any known method. For example, oxygen can be introduced by direct injection, agitation or a combination of direct injection and agitation. When direct injection is used, oxygen can be introduced in gaseous form, liquid form or a combination of the two.

The bioreactor may also have a means for regulating the pH of the medium. The pH of the medium may be lowered by the addition of an acid or increased by addition of a base. The acid or base may be introduced in liquid form, gaseous form, solid form or some combination thereof. In controlling the pH, strong acids may be used, weak acids may be used, strong bases may be used, weak bases may be used or any combination thereof. Any acid or base that is compatible with the algae being grown can be used. In one embodiment, pH is controlled by the addition of glacial acetic acid. Acetic acid is useful because it can be converted into acetate which can serve as an energy and carbon source for the algae. In one embodiment, the pH of the medium is maintained between about 6.0 and about 10.0, between about 6.0 and about 9.0, between about 6.0 and about 8.0 or between about 6.0 and about 7.0. In other embodiments, the pH of the medium is maintained between a pH of about 6.4 and 7.2, between about 6.45 and about 7.15, between about 6.5 and about 7.1, between about 6.55 and about 7.05, between about 6.6 and about 7.0, between about 6.65 and about 6.95, between about 6.7 and about 6.9, or between about 6.75 and about 6.85. In one embodiment the pH of the medium is maintained at pH 6.5±0.1, pH 6.8±0.1 or pH 7.0±0.1.

In one embodiment, the algae can be grown, for example, in small scale laboratory culture systems. Small scale laboratory systems refer to cultures in volumes of less than about 6 liters. In an aspect, the small scale laboratory culture may be 1 liter, 2 liters, 3 liters, 4 liters, or 5 liters. In another aspect of the invention, the small scale laboratory culture may be less than one liter. In an aspect, the small scale laboratory culture may be 100 milliliters or less.

As will be apparent to one of skill in the art, the volume of the culture will depend on the amount of algal biomass desired. The volume is limited only by the size of the bioreactors available to the artisan. In one embodiment, the bioreactors may be of volumes of greater than about 5 liters, or greater than about 10 liters, or greater than about 20 liters. Large scale growth can also be growth of cultures in volumes of 50 liters or more, 100 liters or more, 200 liters or more, 300 liters or more, 400 liters or more, 500 liters or more, 600 liters or more, 700 liters or more, 800 liters or more, 900 liters or more, 1000 liters or more, 2000 liters or more, 3000 liters or more, 4000 liters or more, 5000 liters or more, 6000 liters or more, 7000 liters or more, 8000 liters or more, 9000 liters or more, or 10000 liters or more.

The present disclosure further provides for very large scale culture systems. In one aspect, the volume of culture may be at least 20,000 liters. In another aspect, the volume of culture can be up to 40,000 liters. In another aspect, the volume of culture can be up to 80,000 liters, up to 100,000 liters, up to 125,000 liters, up to 150,000 liters, or up to 175,000 liters. In another aspect, the volume of the culture can be up to 200,000 liters. In another aspect, the volume of the culture can be up to 250,000 liters. In another aspect, the volume of the culture can be up to 500,000 liters. In another aspect, the volume of the culture can be up to 600,000 liters. In another aspect, the volume of the culture can be up to 1,000,000 liters.

As will also be apparent to one of skill in the art, when larger culture volumes are used, it may be necessary to grow the inoculum through several intermediate volumes. The following is a general discussion of methods to scale up a culture. It is well within the abilities of one of ordinary skill in the art to modify the methods discussed herein to accommodate different size starting cultures and different size production cultures. For purposes of this exemplary discussion the starting material is a TAP plate streak with the desired strain or strains of algae. Using a sterile loop algae is removed from the TAP plate and added to a sterile, baffled, 500 mL shake flask containing 150 mL of suitable culture medium and cultured for approximately 5 days at room temperature (about 20-28° C.) with shaking at 150 rpm.

Figure 8:
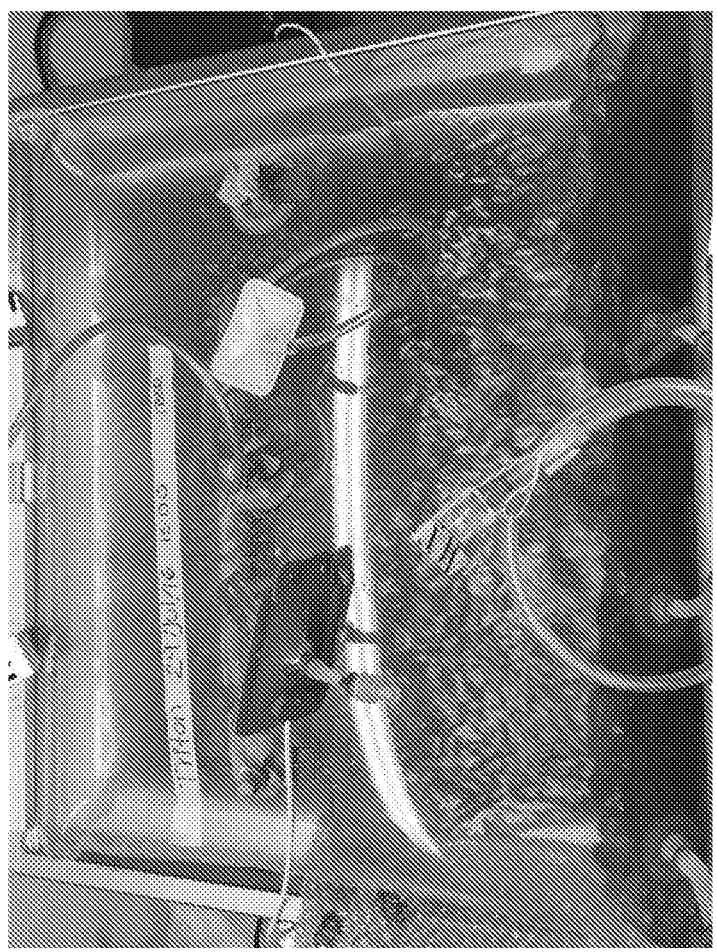
FIG. 8 is a photograph of a wave bag.
Figure 9:
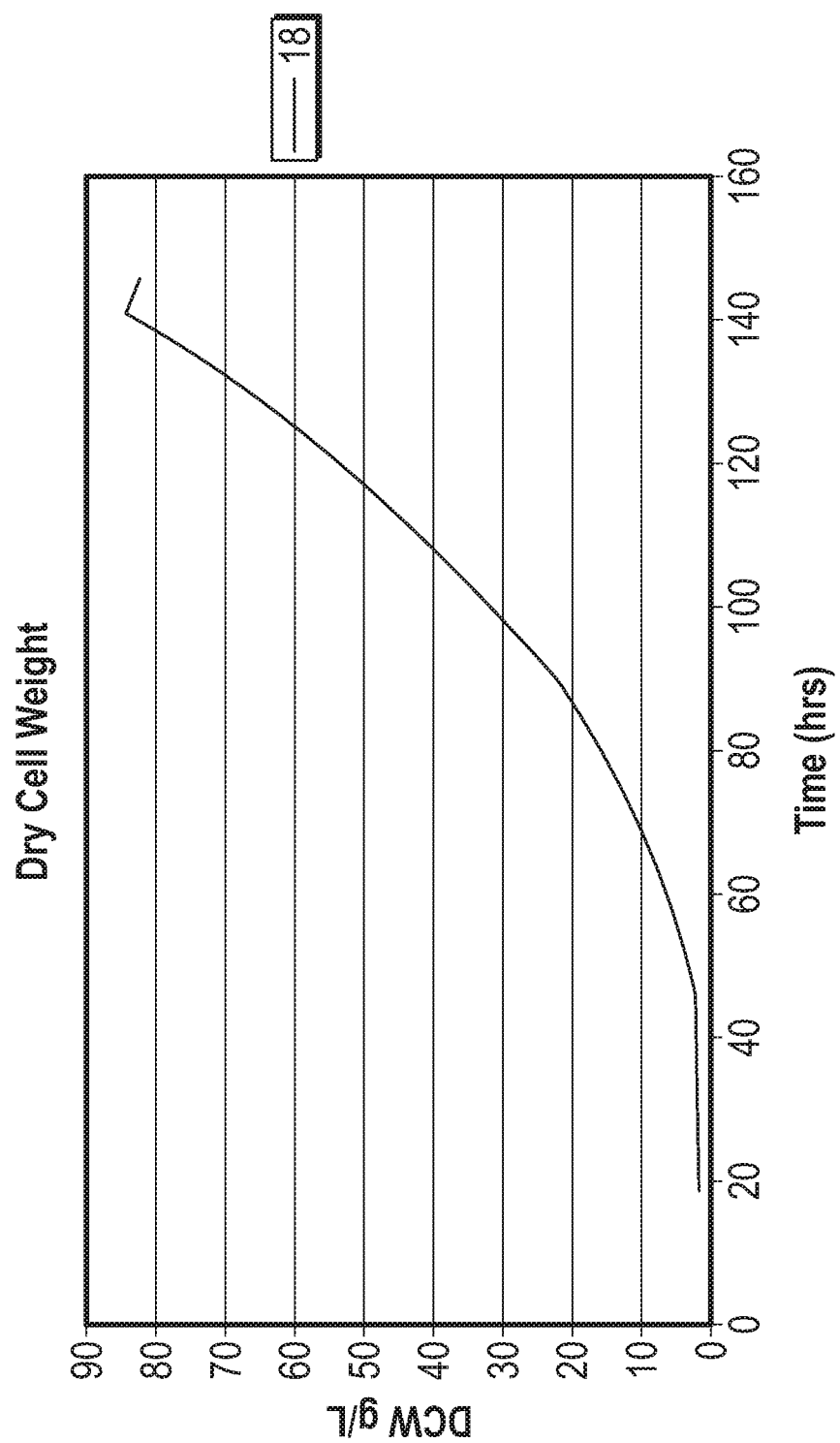
FIG. 9 represents the dry cell weight and growth rate achieved during a fermentation processes using a base media composed of elements in Table 4, trace elements composed of elements in Table 5, and feed media composed of compounds listed in Table 6.

Alternatively, intermediate cultures can be conducted in wave bags. A wave bag is a sterile plastic bag with one or more ports that allow gas exchange (with the atmosphere or introduced gases), sampling, and/or nutrient supplementation (see FIG. 8). The culture conditions, including agitation, for the wave bag are the similar as for a shake flask, but may involve movement other than rotational. One of skill in the art will be able to envision other appropriate vessels for intermediate cultures.

Typically, the culture takes place in the absence of light, but this is not essential. Approximately 2 days before the next scale-up a sample is aseptically obtained to check for contamination as well as proper morphology of the algae. After 5 days of culture, the dry cell weight (DCW) of the flask is typically between 1.0 and 3.0 g/L. Methods for determining DCW are provided herein. Approximately 20% (in this case 120 mL) of the contents of the 500 mL flask is then added to a sterile, baffled 3 L shake flask containing approximately 1050 mL of culture medium for a final volume of approximately 1200 mL or a 1:10 dilution. The 1200 mL culture is cultured in the same manner as the 150 mL culture including the morphology and contamination check. The shake-flask process is continued until a culture that is at least 10% of the volume to be used in a production bioreactor is obtained.

Once enough algae have been grown in shake flasks, the algae can be used to inoculate a bioreactor. For the purposes of this disclosure, bioreactor culture is differentiated from shake flask culture in that in bioreactor culture the culture is fed by the addition of concentrated medium. The bioreactor is inoculated with a volume of culture not exceeding approximately 10% of the initial volume of medium in the bioreactor. The concentration of algae used for inoculation of the bioreactor should be between about 0.1 g/L and about 15 g/L dry cell weight (DCW). In certain embodiments the concentration of algae transferred is between about 0.1 g/L and about 10 g/L, between about 0.1 g/L and about 5 g/L, between about 0.1 g/L and about 4 g/L, between about 0.1 g/L and about 3 g/L, between about 0.1 g/L and about 2 g/L, between about 0.1 g/L and about 1 g/L, between about 0.1 g/L and about 0.9 g/L, between about 0.1 g/L and about 0.8 g/L, between about 0.1 g/L and about 0.7 g/L, between about 0.1 g/L and about 0.6 g/L, between about 0.1 g/L and about 0.5 g/L, between about 0.1 g/L and about 0.4 g/L, between about 0.1 g/L and about 0.3 g/L, and between about 0.1 g/L and about 0.2 g/L. In one embodiment, the following formula is used to calculate the concentration of algae to be used to inoculate the bioreactor:

$$C_{in} = \frac{(V_{br} + 0.1V_{br})C_{br}}{0.1V_{br}}$$

where $C_{in}$ is the concentration of the inoculum, $V_{br}$ is the initial volume medium in the bioreactor and $C_{br}$ is the initial concentration of algae in the bioreactor immediately after inoculation.

The medium (fermentation medium) used to grow the algae in the bioreactorcan be any medium that is suitable for heterotrophic culture of the strain or strains of algae to be grown in the bioreactor. In one embodiment, the composition of the fermentation medium is that given in Table 1.

TABLE 1

Fermentation Medium A

| Chemical Name | Formula | Amount | Units |
|---|---|---|---|
| Ammonium hydroxide | NH$_4$OH | 0.25 | g · L$^{-1}$ |
| Ammonium phosphate monobasic | NH$_4$H$_2$PO$_4$ | 0.1 | g · L$^{-1}$ |
| Potassium phosphate monobasic | KH$_2$PO$_4$ | 0.014 | g · L$^{-1}$ |
| Calcium chloride | CaCl$_2$ | 0.009 | g · L$^{-1}$ |
| Magnesium sulfate heptahydrate | MgSO$_4$·7H2O | 0.0563 | g · L$^{-1}$ |
| Sodium hydroxide | NaOH | 0.04 | g · L$^{-1}$ |
| Trace Elements Solution | Blend | 0.4 | mL · L$^{-1}$ |
| FOAM BLAST ® AntiFoam (optional) | n/a | 0.05 | mL · L$^{-1}$ |
| Adjust pH to 6.0 with glacial acetic acid | | | |

The composition of the trace elements solution is found in Table 2.

TABLE 2

Trace Elements Solution A

| Chemical Name | Formula | Amount | Units |
|---|---|---|---|
| Disodium EDTA dehydrate | Na$_2$EDTA·2H$_2$O | 21.50 | g · L$^{-1}$ |
| Sodium carbonate | Na$_2$CO$_3$ | 3.320 | g · L$^{-1}$ |
| Iron ammonium citrate | (NH$_4$)$_5$Fe(C$_6$H$_4$O$_7$)$_2$ | 5.234 | g · L$^{-1}$ |
| Zinc sulfate monohydrate | ZnSO$_4$·H$_2$O | 0.449 | g · L$^{-1}$ |
| Manganese chloride tetrahydrate | MnCl·4H$_2$O | 1.188 | g · L$^{-1}$ |
| Copper sulfate pentahydrate | CuSO$_4$·5H$_2$O | 0.499 | g · L$^{-1}$ |
| Ammonium heptamolybdate | (NH$_4$)$_6$Mo$_7$O$_{24}$·4H$_2$O | 0.0352 | g · L$^{-1}$ |
| Selenium sulfide | SeS$_2$ | 0.014 | g · L$^{-1}$ |

The fermentation medium and trace elements solutions are sterile solutions to allow for the algal culture in the bioreactors to be free of contamination with other organisms. The fermentation medium may be used as given in Tables 1, 4 and 7 or may be used in a more concentrated form. In certain embodiments the fermentation medium is used at 2×, 3×, 4× or 5× the concentration of the fermentation medium in Tables 4 and 7.

The temperature of the culture within the bioreactor is maintained at a temperature between about 15° C. and about 26° C. or between about 26° C. and about 37° C. In another embodiment the temperature is maintained between about 26.5° C. and about 29.5° C. In still other embodiments the temperature is maintained between about 27° C. and about 29° C. or between about 27.5° C. and about 28.5° C. In one particular embodiment, the temperature of the bioreactor contents is maintained at about 28° C.

During fermentation in the bioreactor, the percent saturation of oxygen in the medium is maintained at between about 5% and 100%. In other embodiments the percent saturation of oxygen is maintained between about 5% and about 90%, between about 5% and about 80%, between about 5% and about 70%, between about 5% and about 60% or between about 5% and about 50%. In other embodiments percent saturation of oxygen is maintained between about 5% and about 55%, between about 10% and about 50%, between about 15% and about 45%, between about 20% and about 40% or between about 25% and about 35%. In another embodiment the percent saturation of oxygen in the medium is maintained at 30%±2.5%. The percent saturation of oxygen in the medium is maintained using any of the methods described herein or that are known in the art.

The range in which the percent saturation of oxygen is allowed to vary during the fermentation (culture) will depend, in part, on the configuration of the bioreactor and in particular its ability to introduce oxygen. Typically the operator will establish a setpoint and associated upper and lower range. The setpoint may be between 5% and 100%. The allowed range may be within any of the ranges provided herein.

A characteristic of the present method is that the algae are fed during fermentation using a feed medium which is a 50×, 60×, 70×, 80×, 90×, 100×, 110× or 120× concentration of the culture medium. Typically, the feed medium is supplemented with a carbon source to support a high growth rate under hetertrophic conditions. Thus in one embodiment, the feed medium is a 100× concentration of a fermentation medium provided herein, supplemented with glacial acetic acid as a carbon source. The composition of one particular feed medium is provided in Table 3.

TABLE 3

Feed Medium A

| Chemical Name | Formula | Amount | Units |
|---|---|---|---|
| Ammonium hydroxide | $NH_4OH$ | 25 | $g \cdot L^{-1}$ |
| Ammonium phosphate monobasic | $NH_4H_2PO_4$ | 10 | $g \cdot L^{-1}$ |
| Potassium phosphate monobasic | $KH_2PO_4$ | 1.4 | $g \cdot L^{-1}$ |
| Calcium chloride | $CaCl_2$ | 0.9 | $g \cdot L^{-1}$ |
| Magnesium sulfate heptahydrate | $MgSO_4 \cdot 7H_2O$ | 5.63 | $g \cdot L^{-1}$ |
| Sodium hydroxide | NaOH | 4 | $g \cdot L^{-1}$ |
| Trace Elements Solution | Blend | 40 | $mL \cdot L^{-1}$ |
| (Glacial) Acetic acid | $CH_3CO_2H$ | 510 | $g \cdot L^{-1}$ |

Feeding of the culture is triggered by changes in pH. As the culture uses acetate to meet its energy needs, the amount of acetic acid in the medium decreases resulting in an increase in the pH of the medium. This increase in the pH is utilized to trigger the addition of feed medium to restore the pH to the desired setpoint. Using this method allows for rapid growth and the attainment of higher culture densities than have been achieved by previous culture systems. Feeding is determined by the operator determining a pH setpoint and a range around which the addition of feed medium is started and stopped. Addition of feed medium will begin when the pH exceeds the setpoint by a certain value and stopped when the pH is below the setpoint by a selected value. As will be appreciated by one skilled in the art, the exact setpoint and range will depend on the particular species of algae being grown. In the case of *Chlamydomonas* sp. the range of pH should not be allowed to drop below pH 5.5 or exceed pH 10. Setpoints for pH will typically be in the range of 6.5 to 7.5 with a range of ±1.0 pH unit. One of skill in the art will appreciate that the pH range may not be symmetrical such that the pH may be allowed to rise to a greater extent than it is allowed to fall. For example, feeding may be initiated when the pH exceeds the setpoint by 0.5 pH units, but cease when the pH decreases below the set point by 0.2 pH units.

It will be appreciated by one of skill in the art that the production of one bioreactor may be used to inoculate another bioreactor. In situations where very large bioreactors are used, it is not feasible to grow inoculum solely in flasks or wave bags. In this case, smaller bioreactors are used to produce the amount of inoculum material necessary to inoculate the final production bioreactor.

In another embodiment, the composition of the fermentation medium is that given in Table 4

TABLE 4

Fermentation Medium B

| Chemical Name | Formula | Amount | Units |
|---|---|---|---|
| Ammonium hydroxide | $NH_4OH$ | 6.25 | $g \cdot L^{-1}$ |
| Potassium phosphate dibasic | $KH_2PO_4$ | 0.75 | $g \cdot L^{-1}$ |
| Calcium chloride | $CaCl_2$ | 0.375 | $g \cdot L^{-1}$ |
| Magnesium sulfate heptahydrate | $MgSO_4 \cdot 7H2O$ | 0.675 | $g \cdot L^{-1}$ |
| Sodium hydroxide | NaOH | 0.083 | $g \cdot L^{-1}$ |
| Trace Elements Solution | Blend | 25 | $mL \cdot L^{-1}$ |
| FOAM BLAST ® AntiFoam (optional) | n/a | 0.05 | $mL \cdot L^{-1}$ |
| Adjust pH to 6.0 with glacial acetic acid | | | |

In another embodiment, the composition of the Trace elements is given in Table 5.

TABLE 5

Trace Elements Solution B

| Chemical Name | Formula | Amount | Units |
|---|---|---|---|
| Disodium EDTA dehydrate | $Na_2EDTA \cdot 2H_2O$ | 21.50 | $g \cdot L^{-1}$ |
| Sodium carbonate | $Na_2CO_3$ | 3.320 | $g \cdot L^{-1}$ |
| Iron ammonium citrate | $(NH_4)_5Fe(C_6H_4O_7)_2$ | 7.1 | $g \cdot L^{-1}$ |
| Zinc sulfate monohydrate | $ZnSO_4 \cdot H_2O$ | 0.449 | $g \cdot L^{-1}$ |
| Manganese chloride tetrahydrate | $MnCl \cdot 4H_2O$ | 6.15 | $g \cdot L^{-1}$ |
| Copper sulfate pentahydrate | $CuSO_4 \cdot 5H_2O$ | 0.4995 | $g \cdot L^{-1}$ |
| Ammonium heptamolybdate | $(NH_4)_6Mo_7O_{24} \cdot 4H_2O$ | 0.0352 | $g \cdot L^{-1}$ |
| Selenium sulfide | $SeS_2$ | 0.014 | $g \cdot L^{-1}$ |

In another embodiment, the composition of the feed media is that given in Table 6.

TABLE 6

Feed Medium B

| Chemical Name | Formula | Amount | Units |
|---|---|---|---|
| Ammonium hydroxide | $NH_4OH$ | 4.6 | $g \cdot L^{-1}$ |
| (Glacial) Acetic acid | $CH_3CO_2H$ | 195.4 | $g \cdot L^{-1}$ |

In another embodiment, the composition of the fermentation medium is that given in Table 7

TABLE 7

Fermentation Medium C

| Chemical Name | Formula | Amount | Units |
|---|---|---|---|
| Ammonium hydroxide | $NH_4OH$ | 6.25 | $g \cdot L^{-1}$ |
| Potassium phosphate dibasic | $KH_2PO_4$ | 0.15 | $g \cdot L^{-1}$ |
| Calcium chloride | $CaCl_2$ | 0.375 | $g \cdot L^{-1}$ |
| Magnesium sulfate heptahydrate | $MgSO_4 \cdot 7H2O$ | 0.675 | $g \cdot L^{-1}$ |
| Sodium hydroxide | NaOH | 0.083 | $g \cdot L^{-1}$ |
| Trace Elements Solution | Blend | 25 | $mL \cdot L^{-1}$ |
| FOAM BLAST ® AntiFoam (optional) | n/a | 0.05 | $mL \cdot L^{-1}$ |
| Adjust pH to 6.0 with glacial acetic acid | | | |

In another embodiment, the composition of the trace elements is given in Table 8.

TABLE 8

Trace Elements Solution C

| Chemical Name | Formula | Amount | Units |
|---|---|---|---|
| Disodium EDTA dehydrate | $Na_2EDTA \cdot 2H_2O$ | 21.50 | $g \cdot L^{-1}$ |
| Sodium carbonate | $Na_2CO_3$ | 3.320 | $g \cdot L^{-1}$ |
| Iron ammonium citrate | $(NH_4)_5Fe(C_6H_4O_7)_2$ | 7.1 | $g \cdot L^{-1}$ |
| Zinc sulfate monohydrate | $ZnSO_4 \cdot H_2O$ | 0.449 | $g \cdot L^{-1}$ |
| Manganese chloride tetrahydrate | $MnCl \cdot 4H_2O$ | 6.15 | $g \cdot L^{-1}$ |
| Copper sulfate pentahydrate | $CuSO_4 \cdot 5H_2O$ | 0.4995 | $g \cdot L^{-1}$ |
| Ammonium heptamolybdate | $(NH_4)_6Mo_7O_{24} \cdot 4H_2O$ | 0.0352 | $g \cdot L^{-1}$ |
| Selenium sulfide | $SeS_2$ | 0.014 | $g \cdot L^{-1}$ |

In another embodiment, the composition of the feed media is that given in Table 9.

TABLE 9

Feed Medium C

| Chemical Name | Formula | Amount | Units |
|---|---|---|---|
| Ammonium hydroxide | $NH_4OH$ | 4.6 | $g \cdot L^{-1}$ |
| (Glacial) Acetic acid | $CH_3CO_2H$ | 195.4 | $g \cdot L^{-1}$ |
| Potassium phosphate dibasic | $KH_2PO_4$ | 1.25 | $g \cdot L^{-1}$ |

The fermentation medium and trace elements solutions are sterile solutions to allow for the algal culture in the bioreactors to be free of contamination with other organisms. The fermentation medium may be used as given in the tables herein (1× concentration) or may be used in a more concentrated form. In certain embodiments, the fermentation medium is used at 2×, 3×, 4×, 5×, 6×, 7×, or 8× the concentration of the fermentation medium provided in the tables. The feed media may be used as given in the tables herein (1× concentration) or in a more concentrated form. In certain embodiments, the feed media is used at 2×, 3×, 4×, or 5× the concentration of the feed media in the tables. Preferably media or solutions having the same designation are used together, for example Fermentation Medium A is used with Trace Elements Solution A and Feed Medium A.

The use of the methods described herein allow for the production of algal cultures of very high density. Thus the present disclosure provides for an algal culture that under steady state conditions has a concentration of algae of at least 50 g/L dry cell weight. In other embodiments is provided an algal culture with a steady state concentration of at least 55 g/L dry cell weight, at least 60 g/L dry cell weight, at least 65 g/L. dry cell weight, at least 70 g/L dry cell weight, at least 75 g/L dry cell weight, at least 80 g/L dry cell weight, at least 85 g/L dry cell weight, at least 90 g/L dry cell weight, at least 95 g/L dry cell weight, at least 100 g/L dry cell weight, at least 105 g/L dry cell weight, at least 110 g/L dry cell weight, at least 115 g/L dry cell weight, at least 120 g/L dry cell weight or at least 125 g/L dry cell weight, at least 150 g/L dry cell weight, at least 175 g/L dry cell weight or at least 200 g/L dry cell weight. In certain embodiments the culture is a culture of a *Chlamydomonas* sp. In particular embodiments, the culture is a culture of *C. reinhardtii*. As is known in the art, a plot of mass or concentration of an organism versus time will typically result in a sigmoid curve. Steady state is period of relatively modest growth following the inflection point of a sigmoid growth curve. For the purposes of this disclosure, a culture of algae is considered to be under steady state conditions when the concentration of the algae is increasing between about 0.1% and about 10% within a 24 hour period. In other embodiments, steady state refers to the situation in which the concentration of algae in the culture is increasing between about 0.1% and 50%, between about 0.1% and 25%, between about 0.1% and 7%, between about 0.1% and about 5%, between 0.1% and 3% or between 0.1% and 2%. A culture is not considered to be in steady state when the concentration of the culture is decreasing.

Once the culture has reached the desired concentration, the culture can be propagated into other bioreactors or harvested or both. If propagated into additional bioreactors, the inoculation procedure is the same as that described herein. The additional bioreactors may of the same size as the bioreactor from which the inoculum is obtained or may be larger or smaller. It will be apparent to one of skill in the art that propagation and/or harvest can be continuous, batch or semi-batch. In batch mode, the entire culture is either harvested or used for propagation. In continuous mode, small amounts of the culture are removed continuously for either harvest or propagation, while at the same time small amounts of culture medium are added to replace the medium being removed. Semi-batch is between batch and continuous. In semi-batch, a portion, but not all, of the culture is removed at regular intervals for propagation or harvest. As with the continuous mode, in semi-batch a corresponding amount of culture medium is added to replace the culture medium removed.

In certain embodiments, some or all of the material in the bioreactor may be harvested. In one embodiment, all of the material is harvested from the bioreactor once the culture has reached the desired stage of growth, for example, the logarithmic or steady state phase of growth. In another embodiment harvesting may be conducted continuously from the growing or steady state culture of algae. In one aspect, removal of the algae maintains the culture in a logarithmic phase of growth. In another aspect, removal of the algae maintains the culture in a steady state phase. The determination of growth rates and phases of microalgae growth are known in the art. For example, in Sode et al., *J. Biotechnology* (1991) 21:209-217, Torzillo et al., *J. Phycology* (1998) 34:504-510, Jung and Lee, *Biotechnology Progress* (2006) 22:1443-1450, and Vonshak, A. Spirulina Platensis Arthrospira: Physiology, Cell-Biology And Biotechnology. 1997. CRC Press, each of which is incorporated by reference in their entirety Upon removal of some or all of the algae containing medium from the bioreactor it may be desirable to separate the algae from the medium (dewatering). In an embodiment, harvesting includes separating at least 90% of the microalgae from the medium to produce a microalgae depleted liquid. In another embodiment, at least 95% of the microalgae are removed from the medium. In another embodiment, at least 97% of the microalgae are removed from the medium. In another embodiment, at least 99% of the microalgae are removed from the medium. In other embodiments, 50% or more of the microalgae are removed. In another embodiment, 75% or more of the microalgae are removed from the medium. In still another embodiment, 80% or more of the microalgae are removed from the medium. In yet another embodiment, the medium can have less than 30% of the microalgae remaining after harvesting. In a further embodiment, less than 25% of the microalgae remain in the medium after harvesting. In a further embodiment, less than 5% of the microalgae remain in the medium after harvesting. In a further embodiment, less than 2.5% of the microalgae remain in the medium after harvesting. In an embodiment, less than 1% of the microalgae remain in the medium after harvesting.

Separation of the microalgae from the liquid may be accomplished by methods known to one of ordinary skill in the art. In one embodiment, the microalgae may be allowed to settle by gravity and the overlying liquid removed. In another embodiment, the microalgae may be harvested by centrifugation of the microalgae containing culture. In an embodiment, centrifugation of the liquid culture may be performed in batch mode, using a fixed volume centrifuge. In a different embodiment, batch harvesting of the microalgae may be accomplished using a continuous flow centrifuge. In another embodiment, the microalgae may be harvested continuously from the growing culture by continuous flow centrifugation. In other embodiments dewatering may be accomplished by filtration, for example, tangential flow filtration. Filtration may be conducted in either batch or continuous harvest modes. In other embodiments, dewatering may be accomplished by electrophoresis techniques such as electrolytic coagulation and electrolytic flocculation. In still other embodiments, dewatering may be accomplished by flocculation. Flocculation may be accomplished by means of chemical flocculation using synthetic or natural flocculants or by autoflocculation. Methods for inducing flocculation include those that can be found in U.S. Pat. No. 8,969,066 and U.S. Patent Publication No. US 2015/0284673 (application Ser. No. 14/649,524) each of which is hereby incorporated in its entirety by reference. The flocculate may be separated from the culture liquid by gravity, centrifugation, dissolved air flotation (DAF) or any other method known to those of skill in the art. If chemical flocculation is used, in some instances it may be desirable to utilize food grade flocculants. Food grade flocculants are commercially available from a variety of sources.

Upon dewatering, the harvested algae may still contain a considerable amount of liquid. In order to facilitate long term storage, it may be desirable to remove additional liquid by drying. In some embodiments, the algal biomass is dried so that the resulting material is at least 75%, at least 80%, at least 85%, at least 90%, or at least 95% dry cell weight. In other embodiments the algae is dried so that the resulting material contains less than 25%, less than 20%, less than 15%, less than 10% or less than 5% moisture. Drying of the algal biomass may be accomplished by any means known in the art. Exemplary methods of drying include, spray drying, ring drying, paddle drying, tray drying, solar or sun drying, vacuum drying and freeze drying.

Once dried, the algae may be suitable for use as a nutritional supplement or additive for either human consumption or for use as an animal feed. Thus, provided herein is a nutritional supplement or feed additive comprising at least 90%, at least 95%, at least 98% or at least 99% of a *Chlamydomonas* sp. and about 80%±5% or 90%±5% dry cell weight, the nutritional supplement or feed additive also having greater than about 50%±5% crude protein, about 10%±5% crude fat, and less than 5% ash. In some embodiments, the nutritional supplement or additive also comprises at least 0.4% (w/w), at least 0.5% (w/w), at least 0.75% (w/w), at least 1.0% (w/w) or at least 1.25% (w/w) Omega-3 fatty acids. In other embodiments the nutritional supplement or additive contains at least 0.25% (w/w), at least 0.75%, at least 1.25%, at least 1.5% or at least 1.75% Omega-6 fatty acids. In still other embodiment, the nutritional supplement or additive comprises at least 1.25% (w/w), at least 1.75%, at least 2.25% or at least 2.75% Omega-9 fatty acids. The nutritional supplement or additive is further characterized as being free of microbial contamination as determined by the criteria in Table 10.

TABLE 10

| Contamination | Target | Error | Units |
|---|---|---|---|
| Aerobic Plate Count (APC) | <10000 | n/a | $CFU \cdot g^{-1}$ |
| *Escherichia coli* (generic) | n.d. | 0 | $CFU \cdot g^{-1}$ |
| Yeast | <10 | n/a | $CFU \cdot g^{-1}$ |
| Total Coliforms | n.d. | 0 | $CFU \cdot g^{-1}$ |
| Mold count | <30 | n/a | $CFU \cdot g^{-1}$ |
| *Staphylococcus aureus* | n.d. | 0 | $CFU \cdot g^{-1}$ |
| *Salmonella* | negative | 0 | $org \cdot (25\ g)^{-1}$ |

Because the method disclosed herein provides for such high density cultures, the method may be used for the production of algae that have been genetically modified to produce proteins of therapeutic value. In some embodiments, the therapeutic protein is a naturally occurring protein. In other embodiments the therapeutic protein is an exogenous protein. An exogenous nucleic acid, nucleotide, polypeptide, or protein as described herein is defined in relationship to the host organism. An exogenous nucleic acid, nucleotide, polypeptide, or protein is one that does not naturally occur in the host organism or is a different location in the host organism.

Therapeutic proteins are used for the treatment or prevention of a disease or disorder. Therapeutic proteins can be mammalian proteins, for example, human proteins. The therapeutic proteins can be used for veterinary care or for human care. Therapeutic proteins can be used for to treat companion, domestic, exotic, wildlife and production animals. The therapeutic proteins can be involved in, for example, cell signaling and signal transduction.

Examples of therapeutic proteins are antibodies, transmembrane proteins, growth factors, enzymes, immunoregulatory, or structural proteins. The therapeutic protein can be a protein found in an animal, or in a human, or a derivative of a protein found in an animal or in a human. Examples of the use of algae to produce therapeutic proteins can be found, for example, in *Proc. Natl. Acad. Sci. USA* (2003) 100:438-42; *Curr. Opin. Plant Biol.* (2004) 7:159-65; *Vaccine* (2005) 23:1828-32; *Curr. Opin. Biotechnol.* (2007) 18:1-8; *Expert Opin. Biol. Ther.* (2005) 5:225-35; *Biotechnol. Lett.* (2010) 32:1373-83; and International Patent Application Publication WO 2001/063,284.

The nucleotide sequence encoding a therapeutic protein of interest can be the naturally occurring or wild-type sequence or can be a modified sequence. Types of modifications include, the deletion of at least one nucleic acid, the addition of at least one nucleic acid, or the replacement of at least one nucleic acid. One skilled in the art will know how to make modifications to the nucleotide sequence.

One particular type of modification that can be made to a nucleotide sequence is codon optimization. As is known in the art, one or more codons of an encoding polynucleotide can be "biased" or "optimized" to reflect the codon usage of the host organism. For example, one or more codons of an encoding polynucleotide can be "biased" or "optimized" to reflect chloroplast codon usage or nuclear codon usage. Most amino acids are encoded by two or more different (degenerate) codons, and it is well recognized that various organisms utilize certain codons in preference to others. "Biased" or codon "optimized" can be used interchangeably throughout the specification. Codon bias can be variously skewed in different plants, including, for example, in algae as compared to tobacco. Generally, the codon bias selected reflects codon usage of the organism (or organelle therein) which is being transformed with the nucleic acid. A polynucleotide that is biased for a particular codon usage can be synthesized de novo, or can be genetically modified using routine recombinant DNA techniques, for example, by a site directed mutagenesis method, to change one or more codons such that they are biased for chloroplast codon usage. Such preferential codon usage, which is utilized in chloroplasts, is referred to herein as "chloroplast codon usage." Examples of chloroplast and nuclear codon usage for *C. reinhardtii* can be found in the art, for example in U.S. Patent Application Publication No.: 2004/0014174 and International Patent Publication No, WO 2011/063,284.

Expression of therapeutic proteins in algae is achieved by the use of an expression vector. An expression vector is a vector designed so that a coding sequence inserted at a particular site will be transcribed and translated into a protein. The expression vector, or a linearized portion thereof, can comprise one or more exogenous nucleotide sequences encoding a therapeutic protein of interest.

Examples of exogenous nucleotide sequences that can be transformed into a host include nucleic acid sequences that code for mammalian proteins. In some instances, an exogenous sequence is flanked by two sequences that have homology to sequences contained in the host organism to be transformed.

Homologous sequences are, for example, those that have at least 50%, at least 60%, at least 70%, at least 80%, at least 90%, at least 95%, at least 98%, or at least 99% sequence identity to a reference amino acid sequence or nucleotide sequence, for example, the amino acid sequence or nucleotide sequence that is found in the host cell from which the protein is naturally obtained from or derived from. Homologous sequences enable recombination of the exogenous sequence into the nuclear or plastid genome of the host algae to be transformed. In some embodiments, the expression vector comprises a polynucleotide operably linked to one or more control elements, such as a promoter and/or a transcription terminator. A nucleic acid sequence is operably linked when it is placed into a functional relationship with another nucleic acid sequence. For example, DNA for a presequence or secretory leader is operatively linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, 2$^{nd}$ Ed., Cold Spring Harbor Press, (1989) and Ausubel et al., *Short Protocols in Molecular Biology*, 2$^{nd}$ Ed., John Wiley & Sons (1992).

A regulatory or control element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, a hairpin structure, an RNAase stability element, an initiation (start) codon, a splicing signal for intron excision and maintenance of a correct reading frame, a STOP codon, an amber or ochre codon, and an IRES. A regulatory element can include a promoter and transcriptional and translational stop signals. Elements may be provided with linkers for the purpose of introducing specific restriction sites facilitating ligation of the control sequences with the coding region of a nucleotide sequence encoding a polypeptide. Additionally, a sequence comprising a cell compartmentalization signal (i.e., a sequence that targets a polypeptide to the cytosol, nucleus, chloroplast membrane or cell membrane) can be attached to the polynucleotide encoding a protein of interest. Such signals are well known in the art and have been widely reported.

In an expression vector, a nucleotide sequence of interest is operably linked to a promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. The promoter can be a constitutive promoter or an inducible promoter. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription.

Many promoters are active in algae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in algae, and antibiotic resistance genes functional in algae include, but are not limited to, those described in e.g., *Curr. Microbiol.* (1997) 35(6):356-62 (*Chlorella vulgaris*); *Marine Biotechnol.* (NY). (2002) 4(I): 63-73 (*Chlorella ellipsoidea*); *Mal. Gen. Genet.* (1996) 252(5):572-9 (*Phaeodactylum tricornutum*); *Plant Mol. Biol.* (1996) 31(1):1-12 (*Volvox carteri*); *Proc. Natl. Acad. Sci. USA*. (1994) 91(24): 11562-6 (*Volvox carteri*); Falciatore A, Casotti R, Leblanc C, Abrescia C, Bowler C, PMID: 10383998, (1999) 1(3):239-251 (Laboratory of Molecular Plant Biology, Stazione Zoologica, Villa Comunale, 1-80121 Naples, Italy) (*Phaeodactylum tricornutum* and *Thalassiosira weissflogii*); *Plant Physiol.* (2002) 129(1):7-12. (*Porphyridium* sp.); *Proc. Natl. Acad. Sci. USA*, (2003) 100(2):438-42. (*Chlamydomonas reinhardtii*); *Proc. Natl. Acad. Sci. USA*. (1990) 87(3): 1228-32. (*Chlamydomonas reinhardtii*); *Nucleic Acids Res.* (1992) 20(12):2959-65; *Marine Biotechnal.* (NY). (2002) 4(1):63-73 (*Chlarella*); *Biochem. Mol. Biol. Int.* (1995) 36(5):1025-35 (*Chlamydomonas reinhardtii*); *J. Microbial.* (2005) 43(4):361-5 (*Dunaliella*); *Marine Biotechnol.* (NY) (1999) 1(3):239-251. (*Thalassiasim* and *Phaedaetylum*); *Appl. Microbial. Biotechnol.* (2002) 58(2): 123-37 (various species); *Mol. Genet. Genomics* (2004) 271(1):50-9 (*Thermo synechocoecus elongates*); *J. Bacteriol.* (2000), 182, 211-215; *FEMS Microbiol. Lett.* (2003) 221(2):155-9; *Plant Physiol.* (1994) 105(2):635-41; *Plant Mol. Biol.* (1995) 29(5):897-907 (*Synechococcus* PCC 7942); *Marine Pollut. Bull.* (2002) 45(1-12): 163-7 (*Anabaena* PCC 7120); *Proc. Natl. Acad. Sci, USA*. (1984) 81(5): 1561-5 (*Anabaena* (various strains)); *Proc. Natl. Acad. Sci. USA*. (2001) 98(7):4243-8 (*Synechocystis*); *Mol. Gen. Genet.* (1989) 216(1): 175-7 (various species); *Mal. Microbial.* (2002) 44(6):1517-31; *Plasmid* (1993) 30(2):90-105 (*Fremyella diplasiphon*); *Gene* (1993) 124: 75-81 (*Chlamydomonas reinhardtii*); *Current Micro.* (1991) 22:15-20; *Current Genet.* (1991) 19: 317-322 (*Chlorella*). Additional promoters can be found in Table 1 of U.S. Pat. No. 6,027,900.

A polynucleotide or recombinant nucleic acid molecule encoding a therapeutic protein can be introduced into an alga cell using any method known in the art. A polynucleotide can be introduced into the cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method" or liposome-mediated transformation.

Microprojectile mediated transformation utilizes microprojeciles such as gold or tungsten, that are coated with the desired polynucleotide by precipitation with calcium chloride, spermidine or polyethylene glycol. The microprojectile particles are accelerated at high speed into a cell using a device such as the BIOLISTIC PD-1000 particle gun (Bio-Rad; Hercules Calif.). Methods for the transformation using biolistic methods are well known in the art (for example, as described in Christou, *Trends in Plant Science* (1996) 1:423-431). Exemplary methods for the transformation of algae can be found in International Patent Application Publication Nos. WO 2011/034,863 and WO 2011/063,284 as well as *Biosci. Biotechnol. Biochem.* (2014) 78:812-7; *J. Biosci. Bioeng.* (2013) 115:691-4; *Proc. Natl. Acad. Sci. USA* (2011) 108:21265-9; and *Plant Physiol.* (2002) 129:7-12; *Adv. Expl. Med. Biol.* (2007) 616:1-9; *Molec. Biotechnol.* (2005) 30:185-91; *Science* (1988) 240:1534-38; *Folia Microbiol.* (2000) 45:496-504; *Plant Physiol.* (2002) 129: 7-12; *Molec. Gen. Genetics* (2000) 263:404-10; *J. Biosci. Bioeng.* (1999) 87:307-14; *Proc. Natl. Acad. Sci. USA* (1990) 87:2087-90; *Plant Cell* (1989) 1:123-32; *Plant Biotechnol. J.* (2007) 5:402-12; and *J. Biotechnol.* (2013) 163:61-8.

The therapeutic protein may be expressed in the nucleus or chloroplast. When nuclear transformation is utilized, the protein can be modified for plastid targeting by employing plant cell nuclear transformation constructs wherein DNA coding sequences of interest are fused to any of the available transit peptide sequences capable of facilitating transport of the encoded proteins into plant plastids, and driving expression by employing an appropriate promoter. Targeting of the protein can be achieved by fusing DNA encoding plastid, e.g., chloroplast, transit peptide sequences to the 5' end of the DNA encoding the protein. The sequences that encode a transit peptide region can be obtained, for example, from plant nuclear-encoded plastid proteins, such as the small subunit (SSU) of ribulose bisphosphate carboxylase, EPSP synthase, plant fatty acid biosynthesis related genes including fatty acyl-ACP thioesterases, acyl carrier protein (ACP), stearoyl-ACP desaturase, beta-ketoacyl synthase and acyl-ACP thioesterase, or LHCPII genes, etc. Plastid transit peptide sequences can also be obtained from nucleic acid sequences encoding carotenoid biosynthetic enzymes, such as GGPP synthase, phytoene synthase, and phytoene desaturase. Other transit peptide sequences are disclosed in *Plant Mol. Biol. Rep.* (1991) 9: 104; *J. Biol. Chem.* 1989 264: 17544; *Plant Physiol.* (1987) 84: 965; *Biochem. Biophys. Res. Commun.* (1993) 196: 1414; and *Science* (1986) 233: 478. Another transit peptide sequence is that of the intact ACCase from *Chlamydomonas* (genbank EDO96563, amino acids 1-33). The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present disclosure are not critical as long as delivery into a plastid is obtained. Proteolytic processing within the plastid then produces the mature protein.

Once the therapeutic protein is expressed it may be administered to a subject. In certain embodiments the therapeutic protein is administered to the subject consuming the algae. In other embodiments, the therapeutic protein is purified or isolated from the algae prior to administration. Several methods are available for purification or isolation of proteins and are known to those of skill in the art. These include precipitation by, for example ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, high performance liquid chromatography (HPLC), electrophoresis under native or denaturing conditions, isoelectric focusing, and immunoprecipitation.

As will be appreciated by one of skill in the art, the exact route of administration will vary depending on such factors as the particular therapeutic protein used, the condition to be treated, and the subject to be treated. Exemplary methods of administration include, but are not limited to, oral, enteral, mucosal, percutaneous, or parenteral. Examples of methods of administration include, oral, intranasal, intratracheal, intravenous, intramuscular, subcutaneous, intraperitoneal, intra-arterial, intrasternal, intralesional, topical, transdermal, inhalation, and iontophoresis. On of ordinary skill in the art can readily determine the most appropriate route of administration based on commonly known factors such as those described herein.

EXAMPLES

The following examples are intended to provide illustrations of the application of the presently claimed invention. The following examples are not intended to completely define or otherwise limit the scope of the claimed invention.

Example 1

Media and Feed Preparation

Unless stated otherwise, all culture media and culture material are sterile. For the purposes of the following examples, sterile is defined as at least a log 16 reduction of *Geobacillus stearothermophilus* spores. Also unless stated otherwise, all materials used are suitable for consumption by humans (food grade).

Trace Elements (TE) Solution. The TE solution is prepared as two separate solutions designated as $TE_A$ (Table 11) and $TE_B$ (Table 12) which are then combined in equal proportion. $TE_A$ is a clear, orange solution, while $TE_B$ is a clear, blue solution. When combined, the resultant solution (TE) is clear and green. All solutions are prepared by adding solid reagents to sterile, deionized water. Reagents should be added to solutions in the order listed in Table 11 and Table 12.

TABLE 11

$TE_A$

| Chemical Name | Formula | Amount | Units |
|---|---|---|---|
| Disodium EDTA dihydrate | $Na_2EDTA \cdot 2H_2O$ | 23.00 | $g \cdot L^{-1}$ |
| Sodium carbonate | $Na_2CO_3$ | 4.64 | $g \cdot L^{-1}$ |
| Iron ammonium citrate | $(NH_4)_5Fe(C_6H_4O_7)_2$ | 10.47 | $g \cdot L^{-1}$ |

TABLE 12

$TE_B$

| Chemical Name | Formula | Amount | Units |
|---|---|---|---|
| Disodium EDTA dihydrate | $Na_2EDTA \cdot 2H_2O$ | 20 | $g \cdot L^{-1}$ |
| Zinc sulfate monohydrate | $ZnSO_4 \cdot H_2O$ | 0.899 | $g \cdot L^{-1}$ |
| Manganese chloride tetrahydrate | $MnCl \cdot 4H_2O$ | 2.376 | $g \cdot L^{-1}$ |
| Copper sulfate pentahydrate | $CuSO_4 \cdot 5H_2O$ | 0.999 | $g \cdot L^{-1}$ |
| Sodium carbonate | $Na_2CO_3$ | 2.00 | $g \cdot L^{-1}$ |
| Ammonium heptamolybdate | $(NH_4)_6Mo_7O_{24} \cdot 4H_2O$ | 0.070 | $g \cdot L^{-1}$ |
| Sodium selenite | $Na_2SeO_3$ | 0.034 | $g \cdot L^{-1}$ |

To prepare the final TE solution, equal volumes of solutions $TE_A$ and $TE_B$ are mixed together. To reduce overall process bioburden, the resulting solution is sterile filtered through a membrane with a 0.22 μm pore size. The final composition of the TE solution is found in Table 2. Any unused TE solution is stored in an opaque container at 2-8° C.

Media Formulation. The medium for the two flask stages, the seed fermentation, and the production fermentation (fermentation medium) is a simple formulation of salts to which is added solution of trace elements (Table 2). The pH medium is adjusted to approximately pH=6.0 using a stock solution of 98% glacial acetic acid. The pH of the medium prior to the addition of acetic acid is approximately 10.5. The medium is sterilized by autoclaving. In this example, the composition of the medium is provided in Table 1. FOAM BLAST® F111-GF AntiFoam is an optional ingredient which is not typically added to the medium when used for flask growth.

The feed for the seed and production fermentations (feed medium) is a concentrated version (100×) of the fermentation medium of Table 1 with a large addition of acetic acid as a primary carbon source. The feed is sterilized by filtration through a membrane filter with 0.22 μm pore size rather than by autoclave to mitigate evaporative loss of the acetic acid. The composition of the feed is found Table 3.

Example 2

Flask Cell Mass Propagation

The following procedure details the creation of one (1) Stage I flask with a total working volume of 150 mL that leads to one (1) Stage II flask with a total working volume of 1,200 mL. More flasks may be prepared as necessary to fulfill seed fermentor inoculation requirements. A general guideline for flask requirements is one (1) liter of Stage II flask broth for every nine (9) liters of media volume in the seed fermentor. The initial flask inoculum may be sourced either from a streaked TAP plate, or from a 1 mL cyrovial (cryobullet).

Stage I. To begin Stage I of flask cell mass propagation, 150 mL of sterile fermentation medium are added in a biological safety cabinet to a sterile, baffled, 500 mL shake flask with a vented closure. For inoculation from a plate, a suitable TAP plate streaked with desired strain of *C. reinhardtii* is obtained and in a biological safety cabinet, a 4 cm streak is taken using a sterile loop and subsequently used to inoculate the prepared Stage I flask.

If a cryobullet is used, this typically adds 192-240 hours to the total Stage I propagation time. The number of cyrobullets desired is removed from a −80° C. freezer and immediately placed in a 500 mL beaker of water at ambient temperature to thaw. Typically 2 cryobullets are used per 50 mL of Fermentation Medium. The beaker containing the cryobullets is quickly placed in water bath at approximately 35° C. to thaw the material in the cryobullets. Once the material in the cryobullets has thawed, the cryobullets are gently shaken to ensure all of the material has liquefied. Once thawed the cryobullets are sprayed and/or wiped with 70% ethanol and the contents of the cyrobullet transferred to a sterile, baffled 500 mL shake flask containing 150 mL of sterile Fermentation Medium. After transfer of the contents of the cryobullet to the shake flask, the shake flask is allowed to remain undisturbed for a period of 1 hour. Once the 1 hour waiting period has elapsed, the shaker flask is wrapped with a material to reduce light exposure, for example a KIMWIPE® and the shake flask transferred to an orbital shaker at ambient temperature (approximately 25° C.) and 150 RPM under a suitable light source of between about 100 to about 500 microeinsteins. After 4 days on the shaker table, the material limiting light exposure is removed and the flask allowed to incubate until a green color is observed, typically by 10 days after the start of the procedure.

The inoculated Stage I flask is then wrapped from the lid down with aluminum foil or some other opaque material and placed on an orbital shaker set to 150 RPM with a throw of 1.9 cm and ambient temperature (typically about 25° C.). The inoculated Stage I flask remains on the orbital shaker for a period of approximately 120 hours. If the Stage I flask was started from a cryobullet, the total shaker time will be approximately 312 to 360 hours (120 hours plus an additional 192-240 hours).

As a check for contamination, 48 hours prior to inoculation of a Stage II flask, a sample is aseptically-removed from the Stage I flask using a sterile pipet in a biological safety cabinet for visual inspection by microscopy and to streak an LB plate (Luria-Bertani plate, see "Molecular Cloning, A Laboratory Manual," Sambrook and Russell, 2001). The LB plate should be streaked with a volume of 1 mL and should be incubated at 37° C. for a period of 24 hours. After 120 hours of Stage I propagation have elapsed, a 1 mL sample is removed aseptically using a sterile pipet in a biological safety cabinet from the Stage I flask for quantification of optical density at 750 nm and dry cell weight concentration (DCW). Methods for the determination of DCW are provided herein. Typical final DCW for a Stage I flask is 1.8-2.5 $g \cdot L^{-1}$, though concentrations up to 3.2 $g \cdot L^{-1}$ are acceptable.

Stage II. The Stage II flask is prepared by adding 1,050 mL of sterile fermentation medium in a biological safety cabinet to a sterile, baffled, 3,000 mL shake flask with a vented closure. The initial working volume for the Stage II flask is 1,200 mL after the addition of the Stage I inoculum. A volume of the final Stage I broth, equal to 10% of the desired initial Stage II working volume (in this case 150 mL), is used to inoculate the prepared Stage II flask in a biological safety cabinet.

The incubation of the Stage II flask proceeds in a similar manner to the Stage 1 flask. The inoculated Stage II flask is wrapped from the lid down with aluminum foil or other opaque material and placed on an orbital shaker set to 150 RPM with a throw of 1.9 cm at ambient temperature (typically about 25° C.). The inoculated Stage I flask remains on the orbital shaker for a period of approximately 120 hours.

As a check for contamination, 48 hours prior to inoculation of the seed fermentor, a sample is aseptically-removed from the Stage II flask using a sterile pipet in a biological safety cabinet for visual inspection by microscopy and to streak an LB plate. The LB plate should be streaked with a volume of 1 mL and should be incubated at 37° C. for a period of 24 hours. Typical final DCW for a Stage II flask is 1.8-2.5 $g \cdot L^{-1}$, although concentrations up to 3.2 $g \cdot L^{-1}$ are acceptable.

Example 3

Seed Fermentation

The seed fermentation is used to produce a much larger amount of cells at a higher DCW concentration than can be achieved in simple shake flasks in order to inoculate the larger production fermentor to the desired initial DCW concentration. The objective of the seed fermentation is to produce at least 30-40 g DCW·L$^{-1}$ in 144-182 h with no detectable contaminants.

Sterile fermentation medium is prepared in a sterile fermentation vessel. The prepared volume of medium should be equal to 90% of the desired starting volume of the seed fermentor to allow for the addition of a 10% (by volume) inoculum. After 120 hours of Stage II flask propagation and verification that no contamination has occurred, a sample from the Stage II flask is aseptically removed using a sterile pipet in a biological safety cabinet and used for quantification of OD$_{750}$ and DCW. As previously stated, typical final DCW for a Stage II flask is 2.5±0.7 g·L$^{-1}$. Once it has been verified that the DCW of the Stage II flask is in the desired range, inoculation of the seed fermentor may proceed.

The desired inoculum volume for the seed fermentors is equal to 10% of the initial seed fermentor working volume and therefore the initial dry cell weight concentration is 0.25±0.07 g/L. The seed inoculum is aseptically transferred in a biological safety cabinet from the flasks to a sterile seed inoculation vessel and then to the seed fermentor. The addition of the inoculum typically causes the pH value to increase above the set point of pH 6.8. If the pH controller is not tuned properly, an excessive amount of the acidic feed may be added to the fermentor during this period resulting in a severe drop in pH. A pH value below 5.5 may adversely affect the performance of the fermentation and should be avoided. To prevent this, the pH control can be temporarily disabled prior to inoculation. If the pH control is disabled, directly after inoculation the pH can be manually adjusted to the set point and the pH control re-enabled. Following a successful inoculation and activation of pH control, an increase in the value of pH should be observed which is indicative of metabolic activity and more specifically, the consumption of acetate.

The seed fermentation is run aerobically with the process parameters and control strategies listed in Table 13. In this example, the seed fermentation is conducted in the absence of light, meaning that any viewing ports present are covered during fermentation.

TABLE 13

Exemplary Seed Fermentation Parameters

| Parameter | Control Strategy | Set point | ±Deviation | Units |
|---|---|---|---|---|
| Total Fermentation Time (TFT) | n/a | 168 | 24 | H |
| Temperature | Set point | 28 | 0.5 | ° C. |
| pH | Set point | 6.8 | 0.2 | pH |
| Airflow | Set point | 1 | 0.1 | Vvm |
| pO$_2$ | Set point | 30 | 3 | % air sat. |
| Pressure | Set point | 0 | 0.01 | Barg |
| Feed Rate | Feedback(pH) | Variable | n/a | g feed/L/h |
| Agitation | Feedback(pO$_2$) | Variable | n/a | RPM |

In this example, the feed stream is a blend of concentrated medium and glacial acetic acid (see Table 3) which is filter sterilized using 0.22 μm pore filter. The feed stream is fed into the fermentor via a peristaltic pump. The acidic feed stream acts to adjust the pH and is dosed automatically by the pH controller when the pH increases above its set point (one-sided "pH-stat"). Dissolved oxygen (DO) is controlled at a set point of 30% air saturation (at atmospheric pressure) by modulating the rate of agitation. If agitation alone becomes insufficient to maintain the DO set point, the sparge rate may also be modulated. In the event of significant foam formation, a sterile antifoam bolus equal to 0.06 mL FOAM BLAST® F111-GF antifoam per liter of broth can be added to the fermentor. For the purposes of this example, "significant foam" is defined as an amount of foam sufficient to "hold-up" the addition of acid from the top of the fermentor. If totalizers/mass flow meters are indicating that acid is being fed, yet no reduction in pH is observed, there is a possibility of "significant foam" formation. In this case, the presence of "significant foam" should be verified by visual inspection through looking glass (which is briefly uncovered for a visual inspection). If foam is allowed to build for too long, there is a possibility that breaking the foam will dump an excessive amount of "held up" acid into the broth resulting in the death of the culture. As such, foam formation should be addressed as soon as possible.

Figure 2:
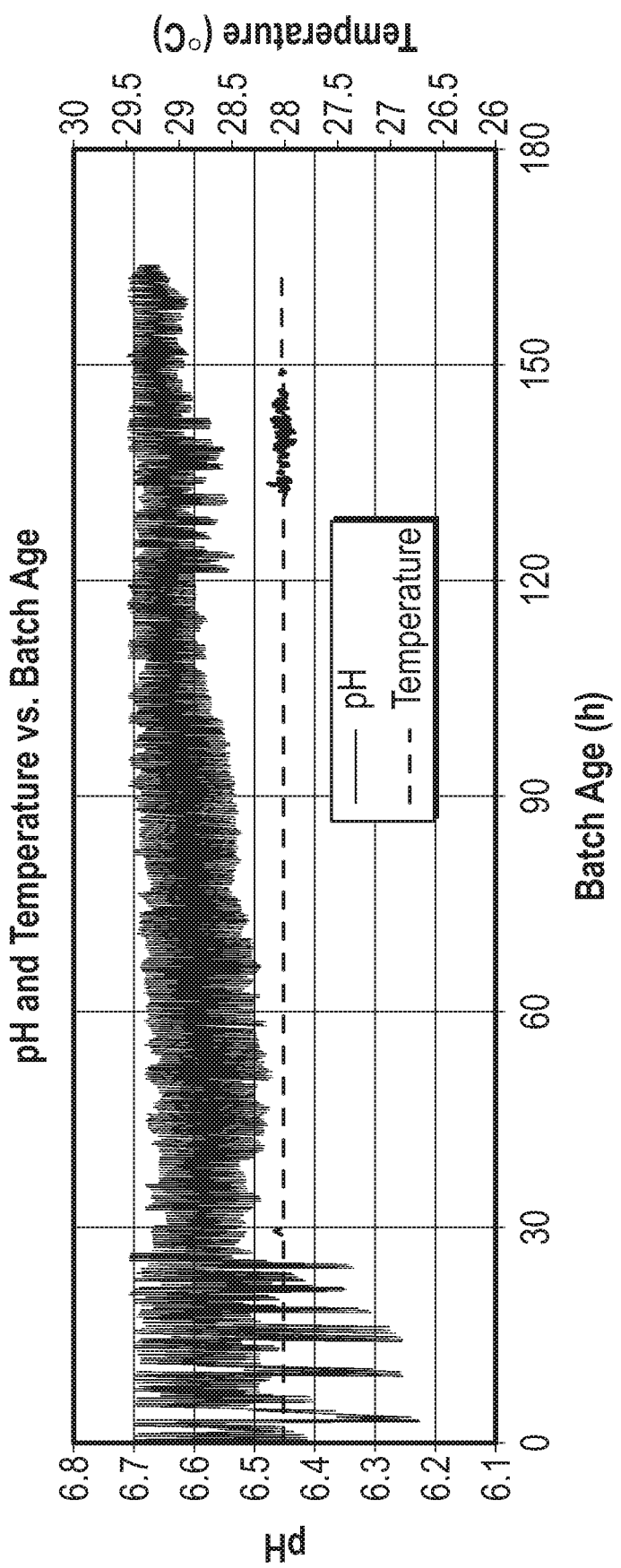
FIG. 2 is a graph of pH and temperature vs. batch age in a seed fermentor.
Figure 3:
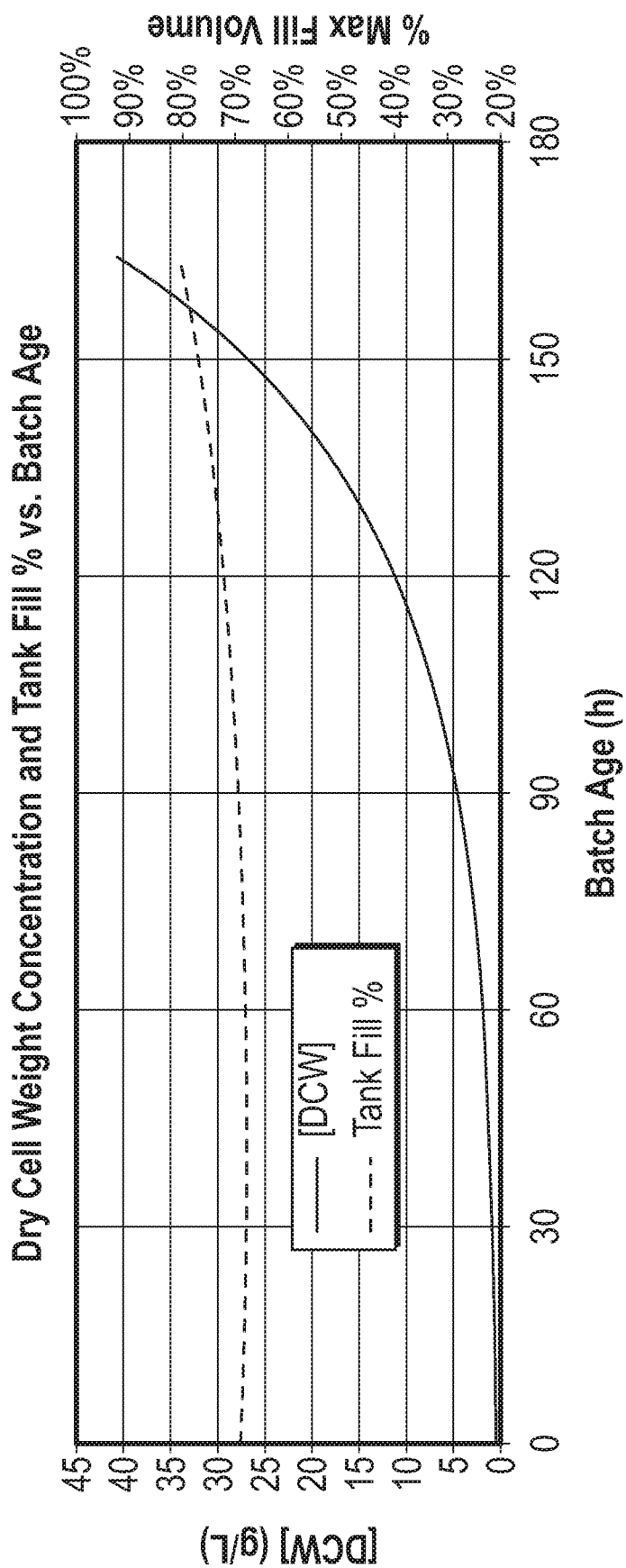
FIG. 3 is a graph of dry cell weight concentration and tank fill percent vs. batch age in a seed fermentor.

Seed fermenters are sampled at a total fermentation time (TFT) of 0, 24, 48, 72, 96, 120, 144, and 168 hours for OD$_{750}$ and DCW. Exemplary results obtained for the various parameters measured can be found in FIGS. 1-3.

Forty-eight hours prior to inoculation of a production fermentor, a sample is aseptically-removed from the seed fermentor through a sterile sampling port for visual inspection by microscopy and to streak on an LB plate (incubate for 24 hours at 37° C.) as a further check for contamination. The harvest criteria for the seed fermentation is a DCW of 30-40 g·L$^{-1}$, although concentrations up to 50.0 g·L$^{-1}$ are acceptable.

Example 4

Production Fermentation

The production fermentation is operated similarly to the seed fermentation; the principal differences between the two processes are the initial concentration of cell mass and the fact that for the production fermentation, the inoculum may come from another fermentor rather than from a shake flask. The objective of the production fermentation is to produce at least 60 g DCW·L$^{-1}$ typically within 90-110 h with no detectable contaminants.

Sterile fermentation medium can be prepared in the fermentation vessel. Alternatively, sterile fermentation medium can be produced outside the fermentation vessel and then introduced into a sterile fermentation vessel. The volume of medium should be equal to 90% of the desired starting volume of the production fermentor to allow for the addition of a 10% (by volume) inoculum.

After completion of seed fermentation and verification that no contamination has occurred, a final sample is removed aseptically through a sterile sampling port for quantification of OD$_{750}$ and DCW. Typical final DCW for the seed fermentation is 30.0-40.0 g/L, though concentrations up to 50.0 g/L are acceptable. Once it has been verified that the DCW of the seed fermentor is in the desired range and that no contamination has occurred, the production fermentor is inoculated.

The desired inoculum volume for the production fermenters is 10% of the production fermentor starting volume and therefore the initial DCW concentration is 3.0-4.0 g/L. For inoculation of the production fermenters in particular, it is preferred that the seed inoculum not be exposed to low-oxygen conditions for longer than 15 minutes. Process control (for example, agitation and sparge) should remain enabled in seed fermentor during transfer of inoculum and residence time in inoculation transfer lines should be minimized as much as possible. Process performance may be substantially reduced if the organism experiences oxygen starvation prior to inoculation.

The addition of the inoculum often causes the pH value to increase above the set point. If the pH controller is not tuned properly, an excessive amount of the acidic feed may be added to the fermentor during this period resulting in a severe drop in pH. A pH value below 5.5 may adversely affect the performance of the fermentation and should be avoided. As such, pH control can be temporarily disabled prior to inoculation. Directly after inoculation, the pH should be manually adjusted to the set point before re-enabling pH control. Following a successful inoculation and activation of pH control, an increase in the value of pH should be observed which is indicative of metabolic activity and specifically the consumption of acetate. The production fermentation is run aerobically with the process parameters and control strategies listed in Table 14. The production fermentation is typically conducted in the absence of light, with all viewing ports covered during fermentation.

TABLE 14

Production Fermentor Process Parameters

| Parameter | Control Strategy | Set point | ±Error | Units |
|---|---|---|---|---|
| Total Fermentation Time | n/a | 100 | 10 | h |
| Temperature | Set point | 28 | 0.5 | ° C. |
| pH | Set point | 6.65 | 0.2 | pH |
| Airflow | Set point | 1 | 0.1 | vvm |
| pO$_2$ | Set point | 30 | 3 | % air sat. |
| Pressure | Set point | 0 | 0.01 | barg |
| Feed Rate | Feedback(pH) | Variable | n/a | g feed/L/h |
| Agitation | Feedback(pO$_2$) | Variable | n/a | RPM |

The feed stream (Feed Medium A, Table 3) is a blend of concentrated medium and glacial acetic acid which is filter sterilized at 0.22 μm and fed into the fermentor via peristaltic pump. The acidic feed stream acts to adjust the pH and is dosed automatically by the pH controller when the pH increases above its set point (one-sided "pH-stat"). The percent saturation of dissolved oxygen (herein abbreviated DO) is controlled at a set point of 30% air saturation (at atmospheric pressure) by modulating the rate of agitation. If agitation alone becomes insufficient to maintain the DO set point, the sparge rate may also be modulated.

In the event of significant foam formation, a sterile antifoam bolus equal to 0.06 mL FOAM BLAST® F111-GF antifoam per liter of broth can be added to the fermentor. For the purposes of this disclosure, "significant foam" is defined as an amount of foam sufficient to "hold-up" the addition of acid from the top of the fermentor. If totalizers/mass flow meters are indicating that acid is being fed, yet no reduction in pH is observed, there is a possibility of "significant foam" formation. In this case, the presence of "significant foam" should be verified by visual inspection through a viewing port and appropriate action taken. If foam is allowed to build for too long, there is a possibility that breaking the foam will dump an excessive amount of "held up" acid into the broth, resulting in the death of the culture. As such, foam formation should be addressed as soon as possible.

Figure 4:
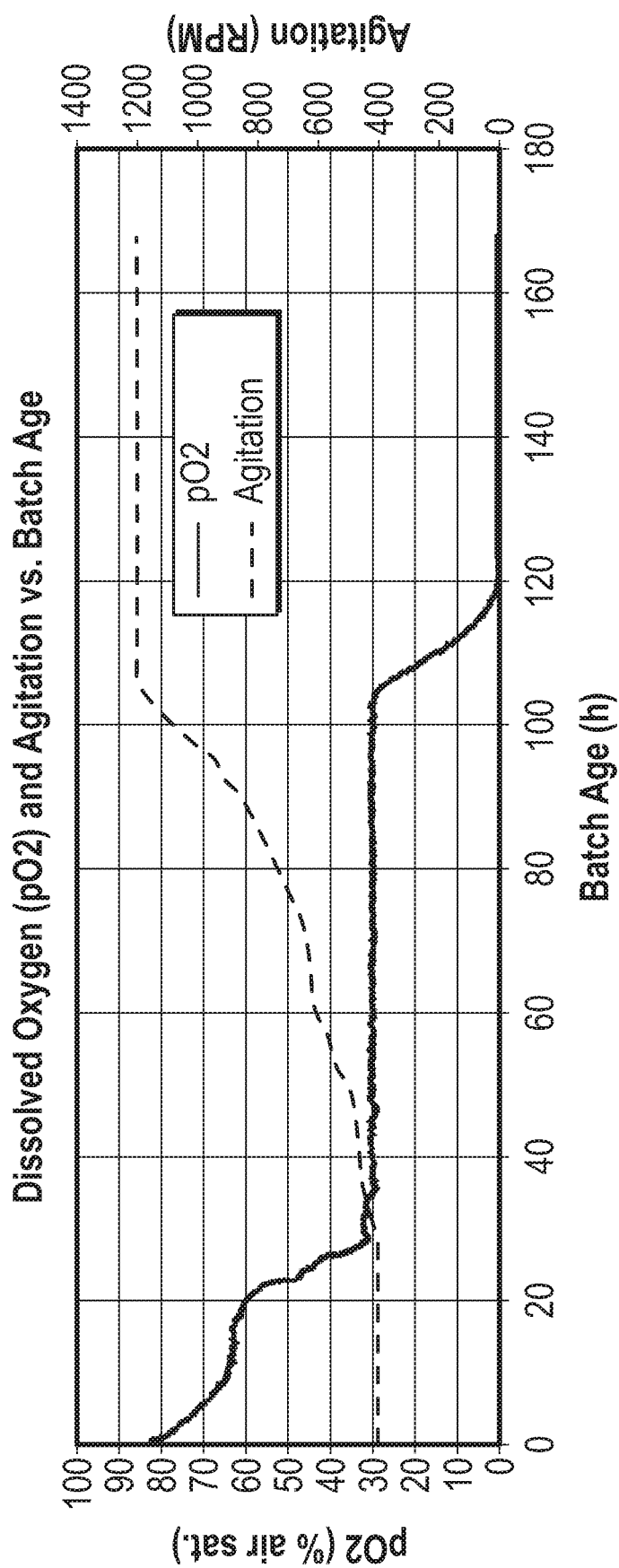
FIG. 4 is a graph of percent saturation of oxygen and agitation vs. batch age in a production fermentor.
Figure 5:
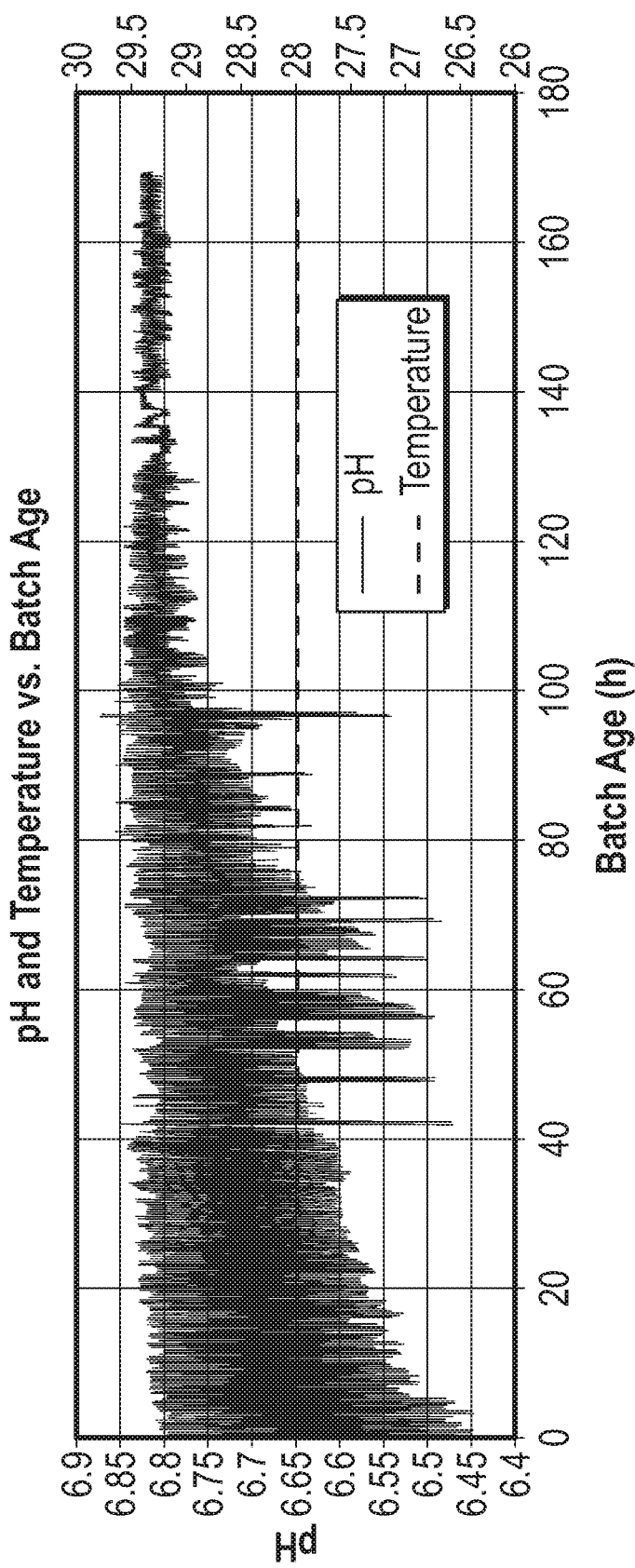
FIG. 5 is a graph of pH and temperature vs. batch age in a production fermentor.
Figure 6:
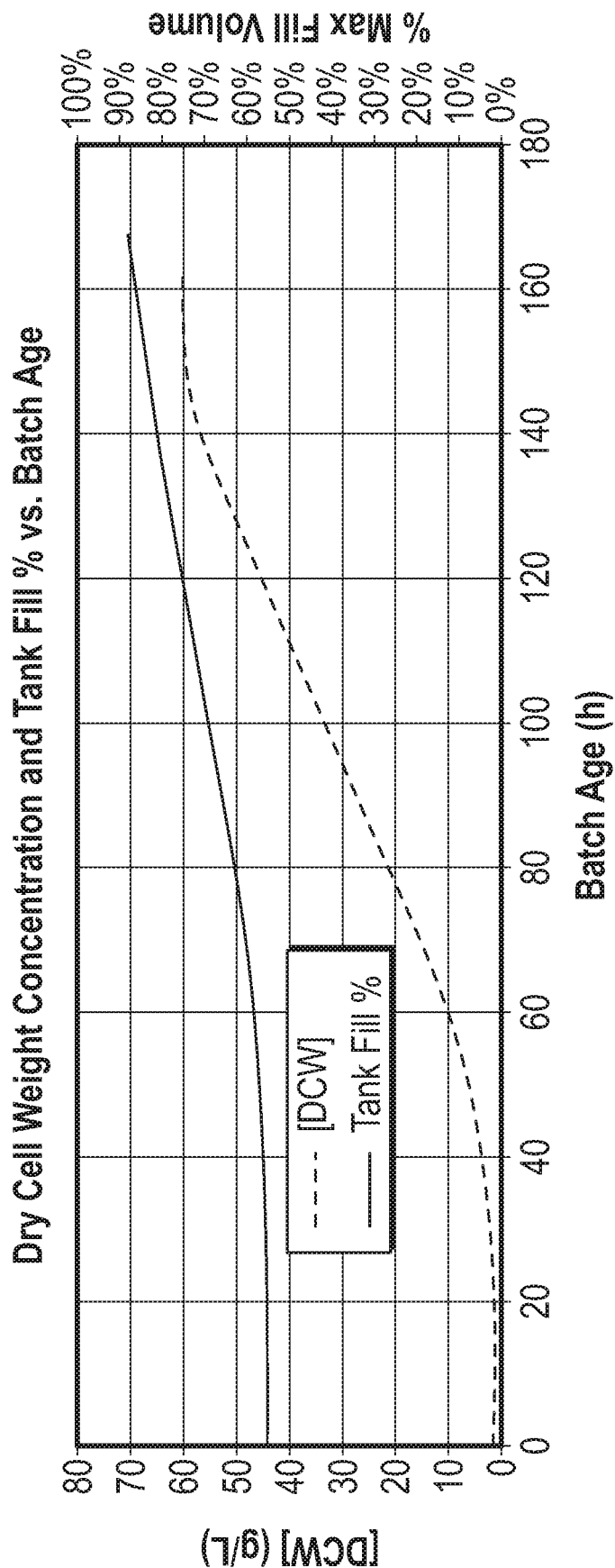
FIG. 6 is a graph of dry cell weight concentration and tank fill percent vs. batch age in a production fermentor.

Production fermentors are sampled at TFT=0, 24, 48, 72, 96, and 100 hours for determination of OD$_{750}$ and DCW. Data and trends for typical 0.5 L production fermentations are shown in FIGS. 4-6. The decrease in pO$_2$ below the set point after approximately 100 hours seen in FIG. 4 is a result of an inability to increase the rate of broth aeration as agitation and sparge have both reached their maximum values in lab-scale fermenters used. Ideal process control would hold the value of DO at its set point throughout the fermentation by increasing sparge rate after agitation has reached its maximum value (cascade control).

The production fermentation, like the seed fermentation, is operated as a one-sided (acid) "pH-stat." As a result of this mode of operation, fluctuations in the value of pH relative to the set point are typically observed throughout the fermentation (see FIG. 5). As the density of the culture increases, the overall acetate consumption rate increases, and the size of the pH "envelope" decreases to a minimum of approximately 0.05 pH units. To maintain fermentation performance, the deviation in pH should preferably not exceed 0.5 pH units, particularly early in the fermentation. If possible, the pH control loop should be tuned to minimize pH deviation as much as possible.

There is no hard target for signaling the end of production fermentation. The overall goal, however, of the production fermentation is to produce as much in-spec algal cell mass as possible given time/equipment constraints. A microwave dry cell weight (DCW) concentration of at least 60 g/L is used as the primary criteria for harvesting a production fermentor.

Example 5

Harvest and Downstream Processing

After completion of production fermentation, broth is transferred from the fermentor for downstream processing unit operations. Final broth should not be inactivated by heating. Algal cell mass is first separated from liquid via centrifugation (approximately 3000 g) at ambient temperature (typically about 25° C.) and the resulting cell mass is then transferred at a solids concentration of approximately 20±5% for spray-drying. The exact conditions for spray drying will vary with the dryer used and the condition of the material. One of skill in the art will readily be able to determine the optimal conditions for spray drying. Spray-dried cell mass is evaluated against specification and if deemed acceptable, packaged in plastic-lined drums. Target criteria for the final, spray-dried algal cell mass product are detailed in Table 15.

TABLE 15

| | Target | Deviation (±) | Units |
|---|---|---|---|
| Visual | | | |
| Appearance | Powder | n/a | n/a |
| Color | Dark Green | n/a | n/a |
| Contamination | | | |
| Aerobic Plate Count (APC) | <10000 | n/a | CFU · g$^{-1}$ |
| Escherichia coli (generic) | n.d. | 0 | CFU · g$^{-1}$ |
| Yeast | <10 | n/a | CFU · g$^{-1}$ |
| Total Coliforms | n.d. | 0 | CFU · g$^{-1}$ |
| Mold count | <30 | n/a | CFU · g$^{-1}$ |
| Staphylococcus aureus | n.d. | 0 | CFU · g$^{-1}$ |
| Salmonella | negative | 0 | org · (25 g)$^{-1}$ |
| Elemental | | | |
| Moisture | 15 | 5 | % |
| Protein (crude) | 50 | 5 | % |
| Fat (crude) | 10 | 5 | % |
| Ash | <5 | n/a | % |
| Nitrogen | 10 | 2 | % |
| Phosphorous (total) | 1 | 0.5 | % |

TABLE 15-continued

| | Target | Deviation (±) | Units |
|---|---|---|---|
| Sodium (total) | 0.5 | 0.3 | % |
| Potassium (total) | 0.15 | 0.1 | % |
| Magnesium (total) | 0.15 | 0.1 | % |
| Calcium (total) | 0.15 | 0.1 | % |
| Sulfur (total) | 0.035 | 0.01 | % |
| Iron (total) | 0.015 | 0.01 | % |
| Manganese (total) | 0.0035 | 0.001 | % |
| Copper (total) | 0.003 | 0.001 | % |
| Zinc (total) | 0.002 | 0.001 | % |

Example 6

Determination of Dry Cell Weight (DCW)

Figure 7:
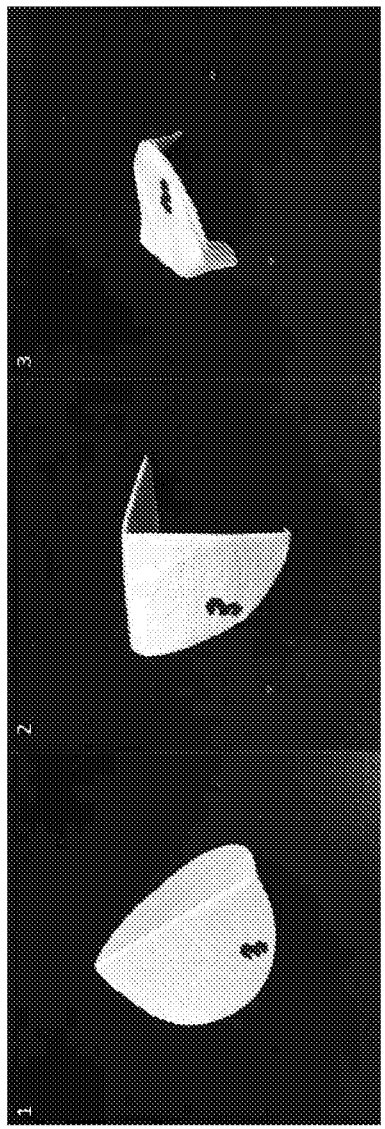
FIG. 7 shows numbering and folding of filters used to determine dry cell weight (DCW) by the microwave method.

A glass microfiber filter is labeled on the underside near the edge using a permanent marker. The labeled filter is then weighed on an analytical balance and the weight recorded in grams ($Mass_{initial,g}$). The pre-weighed filter is then placed in a filtering apparatus and the vacuum applied. The filter is wetted using a solution of 2 g/L ammonium bicarbonate beginning from an edge of the filter and moving across. A known volume of medium containing algae ($Volume_{filtered,ml}$) is added to the filter using a pipet. The volume chosen should not be so much that the filter becomes clogged or the medium runs off the edge of the filter. The pipet is then rinsed with 2 g/L ammonium bicarbonate and the rinse added to the filter. The filter is then rinsed with 2 g/L of ammonium bicarbonate equal to 3 times the $Volume_{filtered,ml}$. The filter is carefully removed from the filter apparatus and folded so the number is in the 7 o'clock position (see FIG. 7). The filter is next folded into quarters and two corners bent down to form legs. The filters are then placed on a microwave safe dish and dried by microwaving at 70% power for 10 minutes. The filters are allowed to cool and then weighed on the same balance used for the $Mass_{initial,g}$ to obtain the $Mass_{final,g}$. The dry cell weight (DCW) is calculated as follows:

$$DCW(g/L) = 1000 \times \frac{Mass_{final,g} - Mass_{initial,g}}{Vol_{filtered,mL}}$$

Example 6

Seed Fermentation Using Fermentation Medium B

Sterile high concentration Fermentation Medium B (Table 4) is prepared in a sterile fermentation vessel. The volume of medium prepared should be equal to 90% of the desired starting volume of the seed fermenter to allow for the addition of a 10% (by volume) inoculum. After 120 hours of Stage II flask propagation and verification that no contamination has occurred, a sample from the Stage II flask is aseptically removed using a sterile pipet in a biological safety cabinet and used for quantification of OD750 and DCW. A typical final DCW for a Stage II flask is 2.5±0.7 g/L. Once it has been verified that the DCW of the Stage II flask is in the desired range, inoculation of the seed fermentor may proceed.

The desired inoculum volume for the seed fermentors is equal to 10% of the initial seed fermentor working volume and therefore the initial dry cell weight concentration is 0.25±0.07 g/L. The seed inoculum is aseptically transferred in a biological safety cabinet from the flasks to a sterile seed inoculation vessel and then to the seed fermenter. The addition of the inoculum typically causes the pH value to increase above the set point of pH 6.8. If the pH controller is not tuned properly, an excessive amount of the acidic feed may be added to the fermentor during this period resulting in a severe drop in pH. A pH value below 5.5 may adversely affect the performance of the fermentation and should be avoided. To prevent this, the pH control can be temporarily disabled prior to inoculation. If the pH control is disabled, directly after inoculation the pH can be manually adjusted to the set point and the pH control re-enabled. Following a successful inoculation and activation of pH control, an increase in the value of pH should be observed which is indicative of metabolic activity and more specifically, the consumption of acetate.

The seed fermentation is run aerobically with the process parameters and control strategies listed in Table 13. In this example, the seed fermentation is conducted in the absence of light, meaning that any viewing ports present are covered during fermentation.

Feed stream is a blend of glacial acetic acid and ammonia (Feed Medium B, Table 6) which is filter sterilized using 0.22 μm pore filter. The feed stream is fed into the fermentor via a peristaltic pump. The acidic feed stream acts to adjust the pH and is dosed automatically by the pH controller when the pH increases above its set point (one-sided "pH-stat"). Dissolved oxygen (DO) is controlled at a set point of 30% air saturation (at atmospheric pressure) by modulating the rate of agitation. If agitation alone becomes insufficient to maintain the DO set point, the sparge rate may also be modulated.

In the event of significant foam formation, a sterile antifoam bolus equal to 0.06 mL. FOAM BLAST® Fill-GE antifoam per liter of broth can be added to the fermentor. For the purposes of this example, "significant foam" is defined as an amount of foam sufficient to "hold-up" the addition of acid from the top of the fermentor. If totalizers/mass flow meters are indicating that acid is being fed, yet no reduction in pH is observed, there is a possibility of "significant foam" formation. In this case, the presence of "significant foam" should be verified by visual inspection through looking glass (which is briefly uncovered for a visual inspection). If foam is allowed to build for too long, there is a possibility that breaking the foam will dump an excessive amount of "held up" acid into the broth resulting in the death of the culture. As such, foam formation should be addressed as soon as possible. Seed fermenters are sampled at a total fermentation time (TFT) of 0, 24, 48, 72, 96, 120, 144, and 168 hours for OD750 and DCW.

Forty-eight hours prior to inoculation of a production fermentor, a sample is aseptically-removed from the seed fermentor through a sterile sampling port for visual inspection by microscopy and to streak on an LB plate (incubate for 24 hours at 37° C.) as a further check for contamination. The harvest criteria for the seed fermentation is a DCW of 40-60 g/L, although concentrations up to 80.0 g/L are acceptable.

Example 7

Production Fermentation Using Fermentation Medium B

The production fermentation using high concentration Fermentation Medium B is operated similarly to the seed fermentation; the principal differences between the two processes are components of the fermentation media, trace elements, and feed media. The objective of the production fermentation using high concentration Fermentation Medium B is to produce at least 60 g DCW/L typically within 90-140 h with no detectable contaminants.

Sterile Fermentation Medium B can be prepared in the fermentation vessel using the recipe detailed in Table 4. Alternatively, sterile fermentation medium can be produced outside the fermentation vessel and then introduced into a sterile fermentation vessel. The volume of medium should be equal to 90% of the desired starting volume of the production fermenter to allow for the addition of a 10% (by volume) inoculum.

After completion of seed fermentation using high concentration fermentation media and verification that no contamination has occurred, a final sample is removed aseptically through a sterile sampling port for quantification of OD750 and DCW. Typically final DCW for the seed fermentation is 40-60 g/L, though concentrations up to 80 g/L are acceptable. Once it has been verified that the DCW of the seed fermenter is in the desired range and that no contamination has occurred, the production fermenter is inoculated.

The desired inoculum volume for the production fermentors is 10% of the production fermentor starting volume and therefore the initial DCW concentration is 4-6 g/L. For inoculation of the production fermenters in particular, it is preferred that the seed inoculum not be exposed to low-oxygen conditions for longer than 15 minutes. Process control (for example, agitation and sparge) should remain enabled in seed fermenter during transfer of inoculum and residence time in inoculation transfer lines should be minimized as much as possible. Process performance may be substantially reduced if the organism experiences oxygen starvation prior to inoculation.

The addition of the inoculum often causes the pH value to increase above the set point. If the pH controller is not tuned properly, an excessive amount of the acidic feed may be added to the fermentor during this period resulting in a severe drop in pH. A pH value below 5.5 may adversely affect the performance of the fermentation and should be avoided. As such, pH control can be temporarily disabled prior to inoculation. Directly after inoculation, the pH should be manually adjusted to the set point before re-enabling pH control. Following a successful inoculation and activation of pH control, an increase in the value of pH should be observed which is indicative of metabolic activity and specifically the consumption of acetate. The production fermentation is run aerobically with the process parameters and control strategies listed in Table 14. The production fermentation is typically conducted in the absence of light, with all viewing ports covered during fermentation.

The feed stream (Feed Medium B, Table 6) is a blend of glacial acetic acid and ammonia which is filter sterilized at 0.22 μm and fed into the fermentor via peristaltic pump. The acidic feed stream acts to adjust the pH and is dosed automatically by the pH controller when the pH increases above its set point (one-sided "pH-stat"). The percent saturation of dissolved oxygen (DO) is controlled at a set point of 30% air saturation (at atmospheric pressure) by modulating the rate of agitation. If agitation alone becomes insufficient to maintain the DO set point, the sparge rate may also be modulated.

In the event of significant foam formation, a sterile antifoam bolus equal to 0.06 mL FOAM BLAST® Fill-GE antifoam per liter of broth can be added to the fermentor. For the purposes of this disclosure, "significant foam" is defined as an amount of foam sufficient to "hold-up" the addition of acid from the top of the fermentor. If totalizers/mass flow meters are indicating that acid is being fed, yet no reduction in pH is observed, there is a possibility of "significant foam" formation. In this case, the presence of "significant foam" should be verified by visual inspection through a viewing port and appropriate action taken. If foam is allowed to build for too long, there is a possibility that breaking the foam will dump an excessive amount of "held up" acid into the broth, resulting in the death of the culture. As such, foam formation should be addressed as soon as possible.

Figure 10:
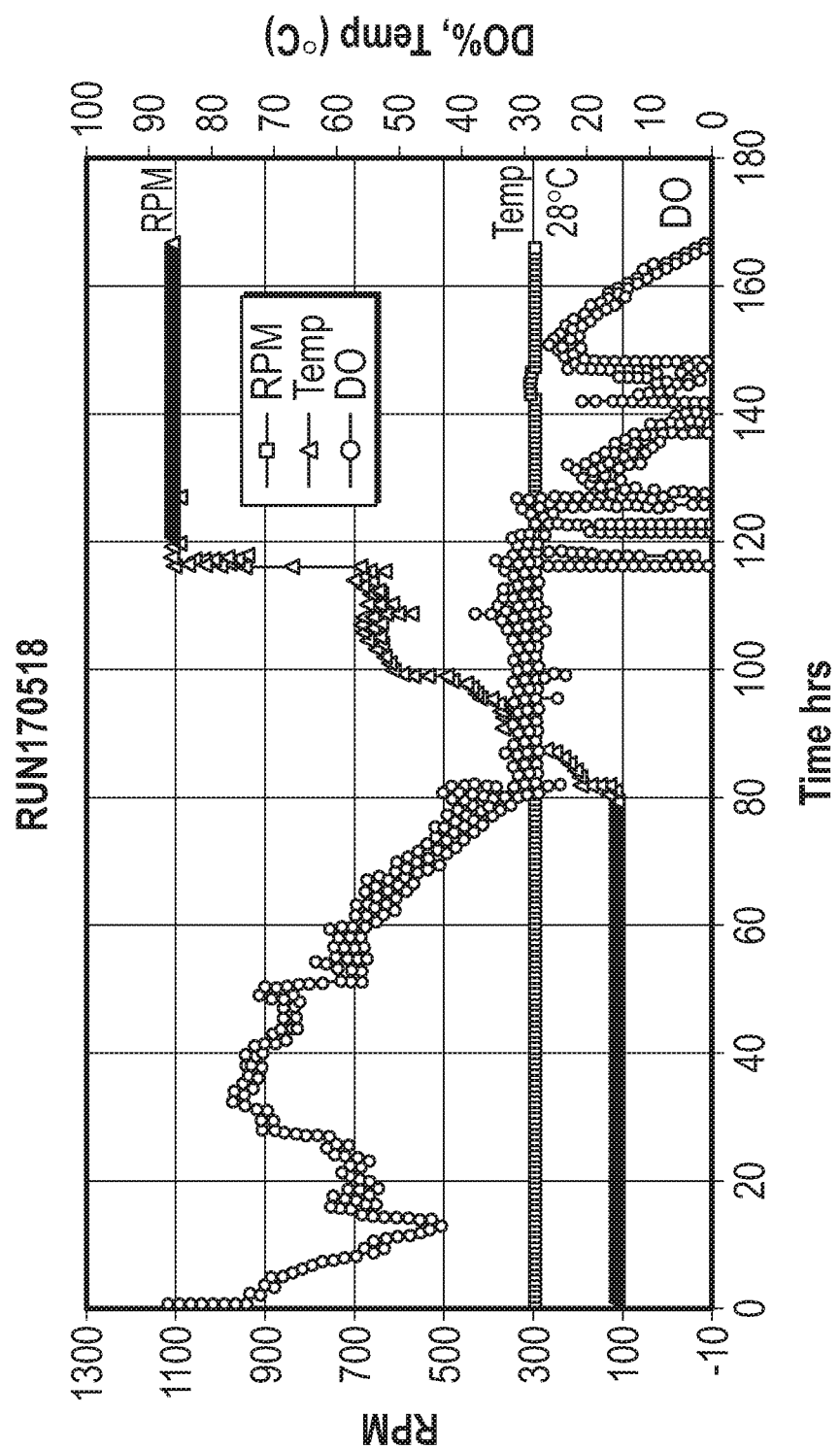
FIG. 10 represents the dissolved oxygen (DO), temperature, and agitation speed of the impellers achieved during a fermentation process using a base media composed of elements in Table 4, trace elements composed of elements in Table 5, and feed media composed of compounds listed in Table 6.

Production fermentors are sampled at TFT=0, 20, 43, 68, 96, 116, and 140 hours for determination of OD750 and DCW. Data and trends for typical 0.5 L production fermentations are shown in FIGS. 9-12. The decrease in pO2 below the set point after approximately 80 hours seen in FIG. 10 is a result of an inability to increase the rate of broth aeration as agitation and sparge have both reached their maximum values in lab-scale fermenters used. Ideal process control would hold the value of DO at its set point throughout the fermentation by increasing sparge rate after agitation has reached its maximum value (cascade control).

Figure 11:
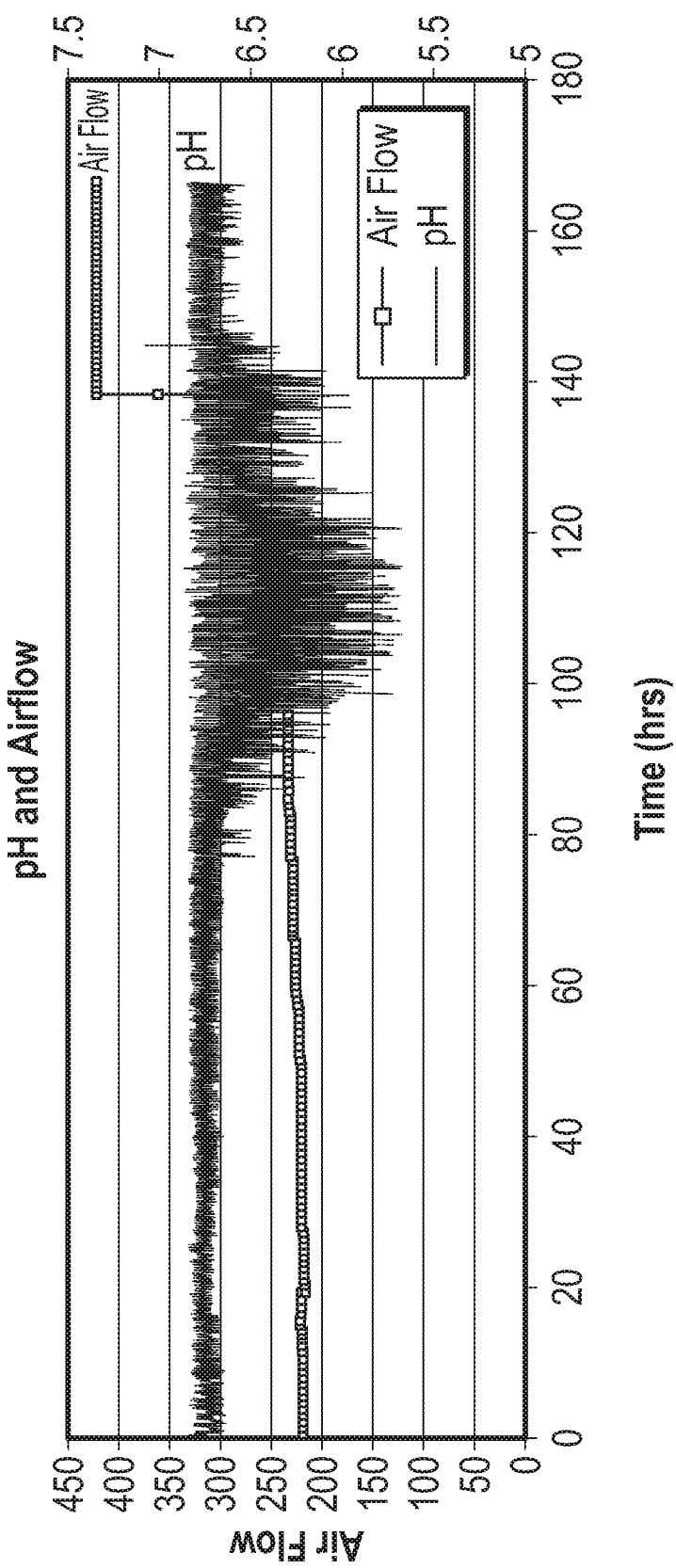
FIG. 11 represents the airflow and pH measured during a fermentation process using a base media composed of elements in Table 4, trace elements composed of elements in Table 5, and feed media composed of compounds listed in Table 6.
Figure 12:
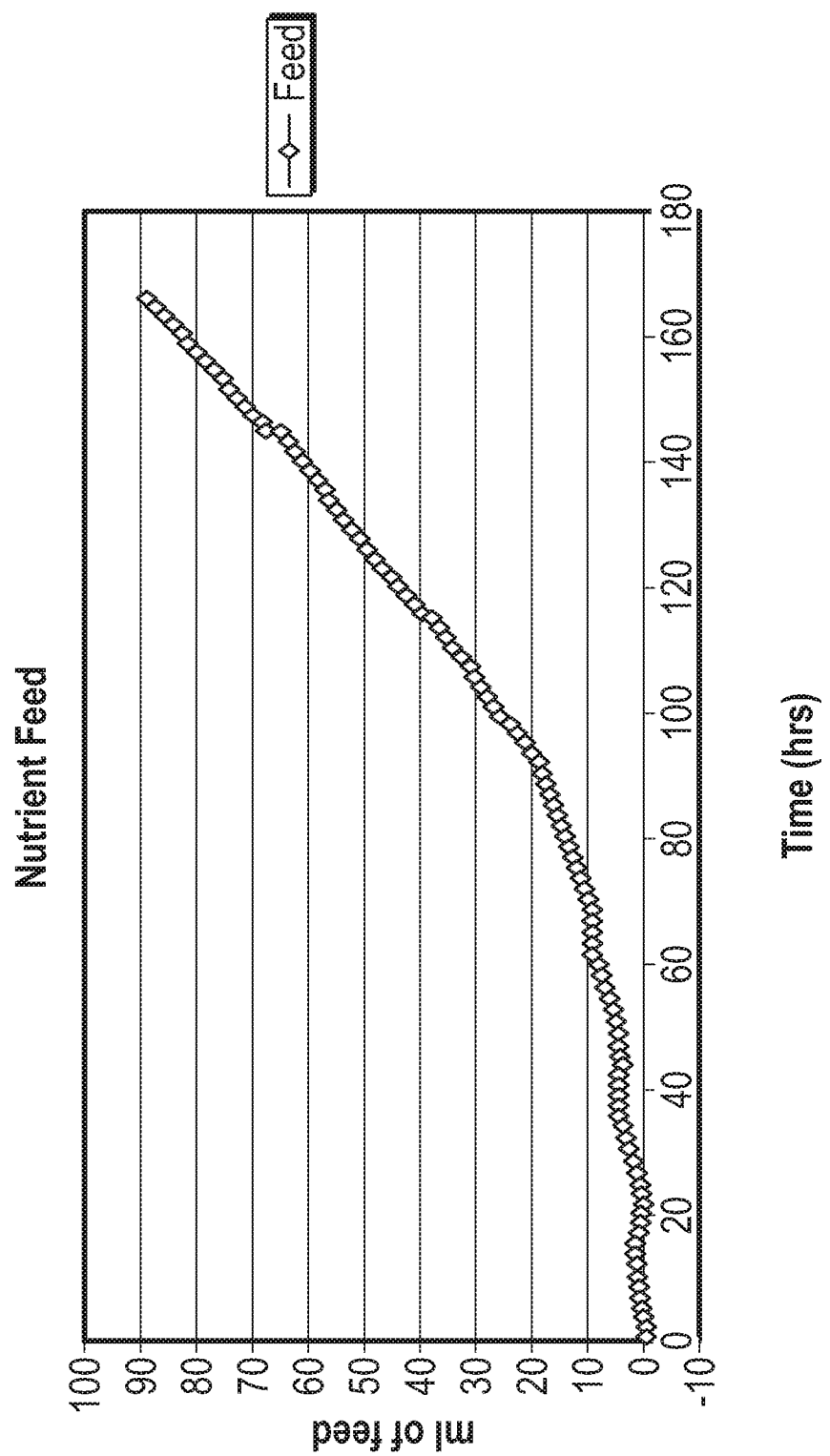
FIG. 12 represents the feed media consumed by a culture of *Chlamydomonas reinhardtii* during a fermentation process using a base media composed of elements in Table 4, trace elements composed of elements in Table 5, and feed media composed of compounds listed in Table 6.

The production fermentation, like the seed fermentation, is operated as a one-sided (acid) "pH-stat." As a result of this mode of operation, fluctuations in the value of pH relative to the set point are typically observed throughout the fermentation (see FIG. 11). As the density of the culture increases, the overall acetate consumption rate increases (FIG. 12). There is no hard target for signaling the end of production fermentation. The overall goal, however, of the production fermentation is to produce as much in-spec algal cell mass as possible given time/equipment constraints. A microwave dry cell weight (DCW) concentration of over 80.0 g/L is demonstrated in FIG. 9.

It is to be understood that the claimed invention has been described in detail by way of illustration and example in order to acquaint others skilled in the art with the claimed invention, its principles, and its practical application. Particular formulations and processes of the claimed invention are not limited to the descriptions of the specific embodiments presented, but rather the descriptions and examples should be viewed in terms of the claims that follow and their equivalents. While some of the examples and descriptions above include some conclusions about the way the claimed invention may function, the inventor does not intend to be bound by those conclusions and functions, but puts them forth only as possible explanations.

It is to be further understood that the specific embodiments set forth above are not intended as being exhaustive or limiting of the claimed invention, and that many alternatives, modifications, and variations will be apparent to those of ordinary skill in the art in light of the foregoing examples and detailed description. Accordingly, the claimed invention is intended to embrace all such alternatives, modifications, and variations that fall within the scope of the following claims.

What is claimed is:

1. A method for aerobic, heterotrophic cultivation of a culture of a *Chlamydomonas* species, the method comprising:
   maintaining a production culture of the *Chlamydomonas* sp. aerobically at a pH set point between 6.0 and 7.0;
   initiating feeding of the production culture by providing acetic acid or acetate as a sole carbon source only when the pH of the production culture exceeds by 0.5 above the set point;

discontinuing the feeding with the carbon source when the pH decreases by 0.2 below the set point;
wherein the pH of the production culture is maintained between 6.0 and 7.0;
growing the production culture until it reaches a density of 50 g/L or more; and
wherein the production culture reaches the density of 50 g/L or more in less than 168 hours.

2. The method of claim 1, wherein the production culture is maintained in the absence of light.

3. The method of claim 1, wherein the pH set point of the production culture is selected from the group consisting of 6.2, 6.3, 6.4, and 6.5.

4. The method of claim 1, comprising growing the production culture until the density is between 50 and 75 g/L.

5. The method of claim 1, comprising harvesting the *Chlamydomonas* sp. from the production culture.

6. The method of claim 5, further comprising drying the harvested *Chlamydomonas* sp.

7. The method of claim 6, further comprising drying the *Chlamydomonas* sp. to a moisture content of less than 15 percent.

8. The method of claim 1, wherein the *Chlamydomonas* sp. is selected from the group consisting of *Chlamydomonas reinhardtii, Chlamydomonas dysomos, Chlamydomonas mundane, Chlamydomonas debaryana, Chlamydomonas moewussi, Chlamydomonas culleus, Chlamydomonas noctigama, Chlamydomonas aulata, Chlamydomonas applanata, Chlamydomonas marvanii, Chlamydomonas proboscigera*, and any combination thereof.

9. The method of claim 8, wherein said *Chlamydomonas* sp. is *Chlamydomonas reinhardtii*.

10. The method of claim 1, wherein the *Chlamydomonas* sp. does not contain a heterologous gene.

11. The method of claim 1, wherein the *Chlamydomonas* sp. contains a heterologous gene.

12. The method of claim 11, wherein the heterologous gene encodes a therapeutic protein and wherein the method further comprises harvesting the therapeutic protein from the production culture.

13. The method of claim 5, further comprising preparing a nutritional supplement or nutritional additive from the *Chlamydomonas* sp. harvested from the production culture.

14. The method of claim 5, wherein said harvesting is by filtration or centrifugation.

15. The method of claim 1, wherein the pH set point of the production culture is 6.5.

16. The method of claim 1, wherein the pH set point of the production culture is 6.2.

17. A method for aerobic, heterotrophic cultivation of a culture of a *Chlamydomonas* species, the method comprising:
maintaining a production culture of the *Chlamydomonas* sp. aerobically at a pH set point of 6.5;
initiating feeding of the production culture by providing acetic acid or acetate as a sole carbon source only when the pH of the production culture exceeds by 0.5 above the set point;
discontinuing the feeding with the carbon source when the pH decreases by 0.2 below the set point;
growing the production culture until it reaches a density between 75 and 100 g/L; and
wherein the production culture reaches the density between 75 and 100 g/L in less than 168 hours.

18. The method of claim 17, further comprising harvesting the production culture and preparing a nutritional supplement or nutritional additive from the *Chlamydomonas* sp. harvested from the production culture.

19. The method of claim 18, wherein the *Chlamydomonas* sp. is selected from the group consisting of *Chlamydomonas reinhardtii, Chlamydomonas dysomos, Chlamydomonas mundane, Chlamydomonas debaryana, Chlamydomonas moewussi, Chlamydomonas culleus, Chlamydomonas noctigama, Chlamydomonas aulata, Chlamydomonas applanata, Chlamydomonas marvanii, Chlamydomonas proboscigera*, and any combination thereof.

20. The method of claim 18, further comprising drying the harvested *Chlamydomonas* sp.

21. The method of claim 18, wherein said *Chlamydomonas* sp. is *Chlamydomonas reinhardtii*.

22. The method of claim 1, comprising growing the production culture until it reaches the density between 75 and 100 g/L.

23. The method of claim 1, comprising growing the production culture until it reaches the density between 100 and 125 g/L.

24. The method of claim 1, comprising growing the production culture until it reaches the density between 125 and 150 g/L.

25. The method of claim 1, comprising growing the production culture until it reaches the density between 150 and 175 g/L.

26. The method of claim 1, comprising growing the production culture until it reaches the density between 175 and 200 g/L.

27. The method of claim 1, wherein the pH set point of the production culture is 6.3.

28. The method of claim 1, wherein the pH set point of the production culture is 6.4.

* * * * *

UNITED STATES PATENT AND TRADEMARK OFFICE
CERTIFICATE OF CORRECTION

| | |
|---|---|
| PATENT NO. | : 11,549,095 B2 |
| APPLICATION NO. | : 16/327642 |
| DATED | : January 10, 2023 |
| INVENTOR(S) | : Robert McBride et al. |

It is certified that error appears in the above-identified patent and that said Letters Patent is hereby corrected as shown below:

On the Title Page

In Item (56), under "Other Publications" in Column 2, Line 1, delete "Clamydomonas" and insert --Chlamydomonas--.

On Page 2, in Item (56), under "Other Publications" in Column 1, Line 2, delete "Fed-Barch" and insert --Fed-Batch--.

On Page 2, in Item (56), under "Other Publications" in Column 2, Line 5, delete "Reinhardtii"" and insert --Reinhardtii."--.

On Page 2, in Item (56), under "Other Publications" in Column 2, Line 6, delete "microalge" and insert --microalgae--.

On Page 2, in Item (56), under "Other Publications" in Column 2, Line 7, delete "14:421 426." and insert --14:421-426.--.

On Page 2, in Item (56), under "Other Publications" in Column 2, Line 20, delete "bioreactor"." and insert --bioreactor",--.

In the Drawings

On Sheet 10 of 12, in figure 10, Line 13, delete "Time hrs" and insert --Time (hrs)--.

In the Specification

In Column 1, Line 55, delete "18:126433)." and insert --18:126-133).--.

In Column 1, Line 56, delete "et al, Plant J." and insert --et al. Plant J--.

Signed and Sealed this
Twenty-eighth Day of February, 2023

Katherine Kelly Vidal
*Director of the United States Patent and Trademark Office*

CERTIFICATE OF CORRECTION (continued)
U.S. Pat. No. 11,549,095 B2

In Column 1, Line 57, delete "Plant J." and insert --Plant J--.

In Column 2, Line 50, delete "dysomos," and insert --dysosmos,--.

In Column 4, Line 17, delete "125 g/L," and insert --125 g/L, 130 g/L,--.

In Column 4, Line 19, delete "195 g/L." and insert --195 g/L--.

In Column 5, Line 40, delete "mixotropic," and insert --mixotrophic,--.

In Column 6, Line 9, delete "dysomos," and insert --dysosmos,--.

In Column 6, Line 65, delete "coil," and insert --coli,--.

In Column 7, Line 2, delete "mixatrophically" and insert --mixotrophically--.

In Column 9, Line 48, delete "bioreactorcan" and insert --bioreactor can--.

In Column 10, Line 25, delete "Tables" and insert --Tables 1,--.

In Column 10, Line 63, delete "hetertrophic" and insert --heterotrophic--.

In Column 11, Line 50, after "4" insert --.--.

In Column 12, Line 33, after "7" insert --.--.

In Column 13, Line 32, delete "65 g/L." and insert --65 g/L--.

In Column 14, Line 27, after "entirety" insert --.--.

In Column 16, Line 60, delete "No," and insert --No.--.

In Column 17, Line 44, delete "RNAase" and insert --RNAse--.

In Column 18, Line 16, delete "Mal." and insert --Mol.--.

In Column 18, Line 29, delete "Biotechnal." and insert --Biotechnol.--.

In Column 18, Line 29, delete "(Chlarella);" and insert --(Chlorella);--.

In Column 18, Line 31, delete "Microbial." and insert --Microbiol.--.

In Column 18, Line 33, delete "(Thalassiasim" and insert --(Thalassiosira--.

In Column 18, Line 33, delete "Phaedaetylum);" and insert --Phaedactylum);--.

CERTIFICATE OF CORRECTION (continued)
U.S. Pat. No. 11,549,095 B2

In Column 18, Line 33, delete "Microbial." and insert --Microbiol.--.

In Column 18, Lines 35-36, delete "synechocoecus" and insert --synechococcus--.

In Column 18, Line 40, delete "Sci," and insert --Sci.--.

In Column 18, Line 44, delete "Mal." and insert --Mol.--.

In Column 18, Line 45, delete "diplasiphon);" and insert --diplosiphon);--.

In Column 18, Lines 60-61, delete "microprojeciles" and insert --microprojectiles--.

In Column 24, Line 17, delete "fermenters" and insert --fermentors--.

In Column 24, Lines 58-59, delete "fermenters" and insert --fermentors--.

In Column 28, Line 35, delete "Fill-GE" and insert --F111-GF--.

In Column 29, Line 65, delete "Fill-GE" and insert --F111-GF--.

In the Claims

In Column 31, Line 26, in Claim 8, delete "dysomos," and insert --dysosmos,--.

In Column 31, Line 28, in Claim 8, delete "moewussi," and insert --moewusii,--.

In Column 32, Line 21, in Claim 19, delete "dysomos," and insert --dysosmos,--.

In Column 32, Line 23, in Claim 19, delete "moewussi," and insert --moewusii,--.